(12) United States Patent
Lafferty et al.

(10) Patent No.: US 8,437,874 B2
(45) Date of Patent: May 7, 2013

(54) TRANSFER STATION FOR PLANT MATERIAL SAMPLING AND TRACKING SYSTEM

(75) Inventors: William Michael Lafferty, Encinitas, CA (US); Scott Wayne Beaver, San Marcos, CA (US); Charles Wilson Tweedy, San Diego, CA (US); Elizabeth Ann George, La Mesa, CA (US); Walter James Frandsen, Jr., Ramona, CA (US); Anthony David Barghini, Encinitas, CA (US); Daniel Steven Kline, Encinitas, CA (US); Shane Scott Swamer, San Diego, CA (US)

(73) Assignee: Syngenta Participations AG, Basel (CH)

( * ) Notice: Subject to any disclaimer, the term of this patent is extended or adjusted under 35 U.S.C. 154(b) by 533 days.

(21) Appl. No.: 12/714,089

(22) Filed: Feb. 26, 2010

(65) Prior Publication Data

US 2011/0213492 A1    Sep. 1, 2011

(51) Int. Cl.
G06F 7/00 (2006.01)
G06K 9/00 (2006.01)
C12Q 1/00 (2006.01)
C12M 1/36 (2006.01)

(52) U.S. Cl.
USPC ........... 700/226; 700/221; 700/223; 700/224; 700/225; 700/227; 700/215; 700/214; 700/218

(58) Field of Classification Search ........................ None
See application file for complete search history.

(56) References Cited

U.S. PATENT DOCUMENTS

| | | | |
|---|---|---|---|
| 5,190,666 A | 3/1993 | Bisconte | |
| 5,332,549 A * | 7/1994 | MacIndoe, Jr. | 422/63 |
| 5,595,707 A | 1/1997 | Copeland et al. | |
| 5,654,200 A | 8/1997 | Copeland et al. | |
| 6,103,518 A | 8/2000 | Leighton | |
| 6,150,158 A | 11/2000 | Bhide et al. | |
| 6,352,861 B1 | 3/2002 | Copeland et al. | |
| 6,659,338 B1 | 12/2003 | Dittmann et al. | |
| 6,763,971 B1 | 7/2004 | Tong | |

(Continued)

FOREIGN PATENT DOCUMENTS

| | | |
|---|---|---|
| FR | 2801380 | 5/2001 |
| GB | 2414700 | 12/2005 |
| JP | 7270429 | 10/1995 |

*Primary Examiner* — Gene Crawford
*Assistant Examiner* — Yolanda Jones
(74) *Attorney, Agent, or Firm* — Dana S. Rewoldt

(57) ABSTRACT

Systems and methods for processing plant material samples and a transfer station designed for use in such systems and methods. In one embodiment, the system includes a controller, a plant-material sampling device, and a transfer station. The plant-material sampling device is configured to communicate with the controller and to read an identifier of a plant. The sampling device also has a removable magazine, and is designed to take at least one plant sample from multiple plants, place such samples in the magazine, and track the identity of the plant from which each sample is taken. The transfer station is configured to hold, at multiple positions, multiple magazines and multiple trays such that the positions of the magazines are mirrored by the positions of the trays, read an identifier of each magazine, read an identifier of each tray, map storage locations for each one of the magazines to storage locations of one of the trays, and sequentially unload plant samples from the magazines to the trays.

15 Claims, 20 Drawing Sheets

U.S. PATENT DOCUMENTS

| | | |
|---|---|---|
| 6,827,901 B2 | 12/2004 | Copeland et al. |
| 6,959,617 B2 | 11/2005 | Deppermann |
| 7,059,207 B2 | 6/2006 | Harris |
| 7,093,508 B2 | 8/2006 | Harris |
| 7,118,918 B2 | 10/2006 | Copeland et al. |
| 7,134,351 B2 | 11/2006 | Deppermann |
| 7,235,055 B2 | 6/2007 | Pfistershammer |
| 7,278,328 B2 | 10/2007 | Massaro |
| 7,454,989 B2 | 11/2008 | Deppermann |
| 7,510,681 B2 | 3/2009 | Justin et al. |
| 7,572,410 B2 | 8/2009 | Chaumat |
| 2007/0093728 A1 | 4/2007 | Douglas et al. |
| 2009/0042180 A1 | 2/2009 | Lafferty et al. |
| 2009/0087830 A1 | 4/2009 | Oostman |
| 2009/0139353 A1 | 6/2009 | Kline et al. |

* cited by examiner

TRANSFER STATION FOR PLANT MATERIAL SAMPLING AND TRACKING SYSTEM

RELATED APPLICATIONS

The present application is related to U.S. application Ser. No. 11/835,986 entitled "System for Sampling and Tracking Plant Material" filed on Aug. 8, 2007, and U.S. application Ser. No. 11/948,491 entitled "Device for Sampling Plant Material" filed on Nov. 30, 2007. The contents of both of these applications are incorporated by reference herein. The present application is being filed as a United States utility application and as an international application under the Patent Cooperation Treaty on the same day.

SUMMARY

The present invention relates to systems and methods for sampling and tracking plant material from a large number of plants. More particularly, the present invention pertains to systems and methods that obtain sample material for use in DNA, RNA, proteins or metabolite analysis applied to discovery, marker-assisted selection, or quality control programs. Even more particularly, the invention relates to methods and systems of transferring samples from collection devices to micro-titre trays (sometimes called "plates") or similar devices so that downstream testing (such as that described above) or other processing may be performed on the samples. Embodiments of the invention are useful in systems designed to obtain genetic marker information from a large number of plants to aid in the selection of plants.

It is well known that genetic markers can be obtained from DNA and used for a variety of purposes. For example, in the field of plant analysis, the DNA obtained from plant material can be analyzed to generate molecular marker information. In this process, DNA sequence variation can be analyzed to discover correlations between molecular markers and traits. Then, plants may be selected for desired traits based on molecular marker information. Traits selected through this process may include, without limitation, agronomic traits such as yield, abiotic-stress tolerance, biotic-stress tolerance, or end-user traits such as plant composition, animal nutrition traits, human health, and the like.

For marker-assisted breeding, seeds of plants with a desired trait are planted in soil either in a greenhouse or in a field. Plant tissue (e.g., a portion of a leaf) is then harvested from the plants for preparation of DNA (once sufficient tissue can be removed from the plants without compromising their viability). Thus, genomic DNA is isolated for further processing to find specific genetic characteristics. In the subsequent processing, these characteristics are linked to traits of interest and are used to predict the presence or absence of the traits of interest in the sampled plants.

As a practical matter, the identification of plants involves complicated procedures that are difficult, if not impossible, to accomplish on-site in the field. The situation becomes further complicated when a large number of plants are involved, such as in a commercial agricultural operation where thousands, or tens of thousands, of different plants are cultivated in the same field. In such operations, the ability to subsequently identify a particular plant is often important.

For a large commercial operation such as the type mentioned above, several factors are considered. For one, all plants in a field need to be properly identified. For another, these identifications need to be accomplished without undue delay. And, finally, each plant that is identified must be capable of being subsequently found at its field location.

In light of the above, it is an object of the present invention to provide a system and method for processing samples of plant material wherein a particular plant in the field can be subsequently found. Another object of the present invention is to provide a system and method for processing samples of plant material wherein plants can be identified and processed. Still another object of the present invention is to provide a system and method for transferring plant samples from a sampling device into trays or similar devices used to carryout DNA and other testing of the plant samples. The results of tests carried out on the plant samples may be used to cultivate those plants that pass the tests or otherwise demonstrate desired characteristics based on the tests.

In one embodiment, the invention provides a system for processing plant material samples, the system including a controller, a plant-material sampling device, and a transfer station. The plant-material sampling device is configured to communicate with the controller and to read an identifier of a plant, having a removable magazine, and for taking at least one plant sample from multiple plants, placing such samples in the magazine, and tracking the identity of the plant from which each sample is taken. The transfer station is configured to hold, at multiple positions, multiple magazines and multiple trays such that the positions of the magazines are mirrored by the positions of the trays, read an identifier of each magazine, read an identifier of each tray, map storage locations for each one of the magazines to storage locations of one of the trays, and sequentially unload plant samples from the magazines to the trays.

In another embodiment, the invention provides a method of processing plant material samples, the method including collecting plant-material samples from a plurality of plants using a plant-material sampling device, transferring the plant material samples to a plurality of trays at a transfer station, performing tests on the plant material samples, and selecting certain of the plants for cultivation based on the tests. The sampling device is configured to communicate with a controller and to read an identifier of a plant, has a removable magazine, and tracks the identity of the plant from which, each sample is taken. The transfer station is configured to hold, at multiple positions, multiple magazines and multiple trays such that the positions of the magazines are mirrored by the positions of the trays, read an identifier of each magazine, read an identifier of each tray, map storage locations for each one of the magazines to storage locations of one of the trays, and sequentially unload plant materials from the magazines to the trays.

In another embodiment, the invention provides a transfer station including multiple magazine positions for holding multiple magazines, and multiple tray positions for holding multiple trays such that the magazine positions are mirrored by the tray positions Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
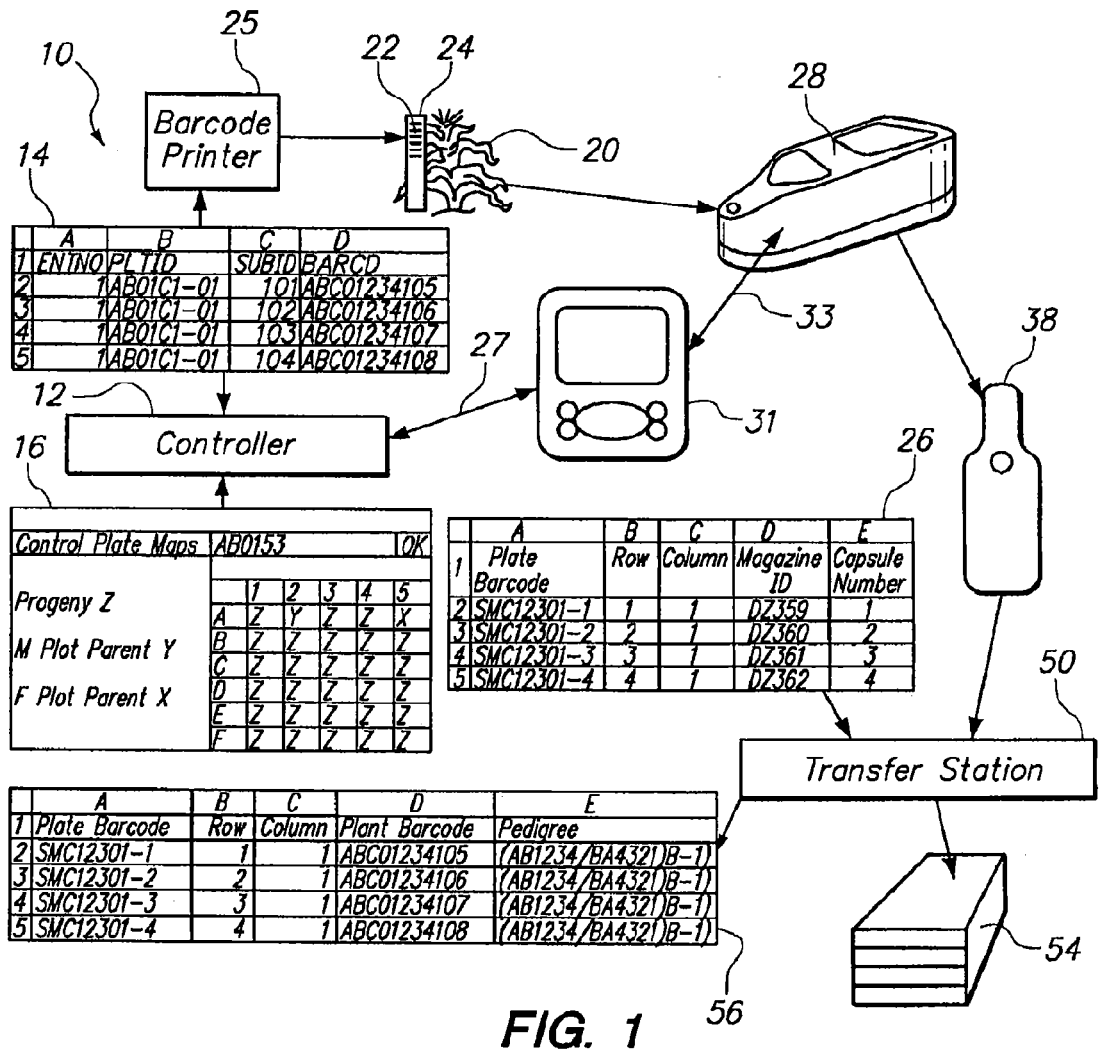
FIG. 1 is a schematic illustration of a system for processing plant samples in accordance with one embodiment of the invention.
Figure 2:
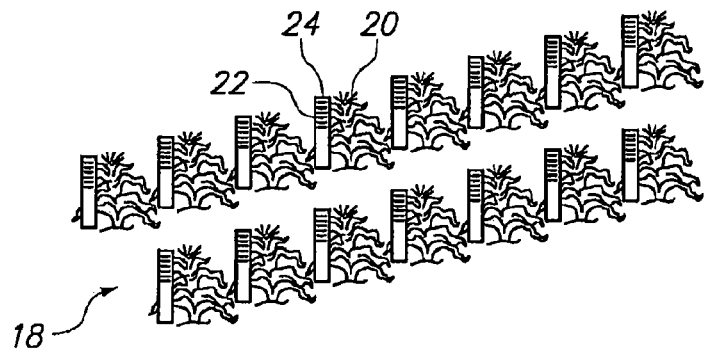
FIG. 2 is a perspective view of a plant field.

Referring initially to FIG. 1, a system in accordance with the present invention is shown and is generally designated 10. As shown, the system 10 includes a controller 12 (e.g., a microprocessor with associated devices such as memory and I/O devices or a computer). The controller includes process management software that receives input from two sources. These sources are: a plant database 14 and a data input table 16. Together, these sources (i.e., database 14 and table 16) provide information for monitoring a large number of plants. For example, consider the field that is shown and generally designated 18 in FIG. 2. In order to monitor the plants 20, each plant 20 must be identifiable. For this purpose, inputs to the controller 12 from database 14 allow the user to document the identity of individual plants, such as the plant 20, as well as the identity of other plants 20 in the field 18. Specifically, the database 14 includes a plurality of virtual plants for use in an experiment. For instance, for an experiment XYZ using 500 plants, the database 14 will include virtual plants XYZ-001 through XYZ-500.

The controller 12 also receives input from the data input table 16. That data may include information about a plant's pedigree or the downstream processing intended for samples from the plant 20, or other data related to the plant 20 including the plant's physical location as determined by global positioning (GPS). For instance, an experiment may require testing of two parent plants 20 and their progeny plants 20. In such a case, the parent plants 20 may be planted in one location while the progeny seeds are planted in another distinct location. Genetic information relating to the parent plants 20 and to the progeny plants 20 may be entered into the data input table 16. Further, instructions for the downstream processing of each type of plant 20 may also be entered into the data input table 16 for use in the handling of samples taken from the plants 20. For instance, the instruction may identify where a sample of the plant 20 should be transferred, how many samples from a plant 20 should be transferred to a particular location, and what testing should be performed on the samples from a plant 20.

In order to identify the plants 20, an identifier or unique feature 22 such as a barcode or RFID, for example, is linked to each plant 20. This unique feature 22 may be pre-fabricated or fabricated in physical form in the field 18 and applied to the plant 20 or to a stake 24 placed into the ground adjacent the appropriate plant 20. As shown in FIG. 1, the system 10 includes a device 25 that receives plant information from the plant database 14 and creates the unique features 22 including plant information. In FIG. 1, the creating device 25 is a barcode printer. Depending on the desired procedure, a different unique feature 22 may be made for each plant 20 or for every certain number of plants 20. Thus, each unique feature 22 effectively provides an address for a respective plant or plants in the field 18. As will be discussed below in more detail, this same information on the unique features 22 is also provided for inclusion with subsequently collected field data and is presented in document form as a work-list 26. In certain embodiments, the work-list 26 includes a list of instructions for the downstream processing of plant samples. Accordingly, the work-list 26 is machine readable, and may be human readable. Typically, the work-list 26 contains information relating to the source of each plant sample, the desired destination of each plant sample, and optimized processing steps involved in moving each plant sample to its desired destination.

A sampling device 28 is provided to collect plant material from selected plants 20 in the field 18. During the collection of samples from plants 20, each plant 20 being sampled is first identified by its unique feature 22. Further, it will be appreciated that the sampling data obtained by the sampling device 28 is communicated to the controller 12. In FIG. 1, this communication is performed by a handheld computer 31 with at least a temporary memory (such as a "Pocket PC.") Specifically, the handheld computer 31 logs the activities of the sampling process and temporarily stores the sampling data for subsequent download to the controller 12 (indicated by arrow 27). It is noted that, while the illustrated system 10 uses a separate handheld computer 31 to provide communication between the sampling device 28 and the controller 12, the sampling device 28 could include memory or data storage that could be downloaded directly to the controller 12 without use of the handheld computer 31 as an intermediary. As indicated by the double-ended arrow 33, the handheld computer 31 also provides a user interface for establishing various sampling options to be performed by the sampling device 28.

Figure 3:
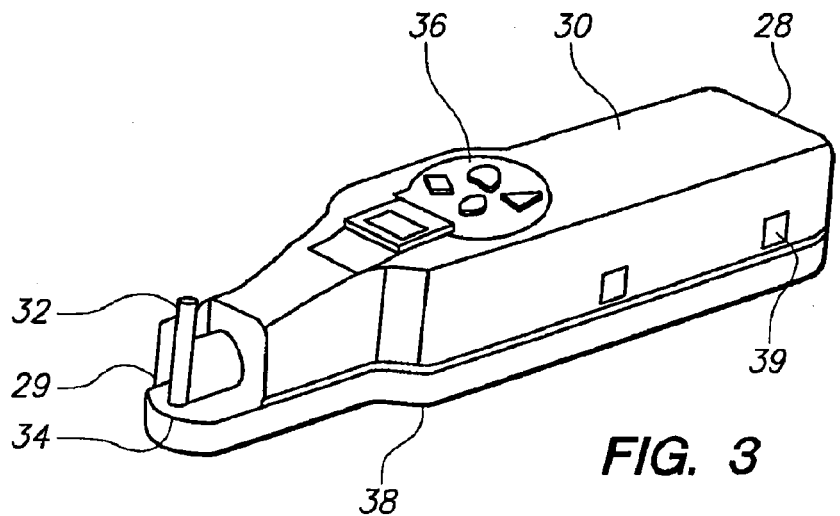
FIG. 3 is a perspective view of a sampling device in accordance with the present invention.

Referring now to FIG. 3, the sampling device 28 is shown to include a housing 30 with a punch 32 and die 34 that are mounted at the front end of the housing 30. A keypad 36 located on the top of the housing 30 is positioned to activate the punch 32 when instructed. Also, the sampling device 28 includes a unit 29, such as a reader or scanner, for retrieving a plant's unique feature 22. In combination, a plant's unique feature 22 and the retrieving unit 29 serve as a means for identifying each plant 20. Thus, whenever, a leaf (not shown) from an identified plant 20 is positioned between the punch 32 and the die 34, and the punch 32 is activated by the keypad 36, a plug (also not shown) is cut from the leaf This plug is deposited into a magazine 38 (or similar container). As shown in FIG. 3, the magazine 38 is engaged with the sampling device 28. This, however, is a selective engagement as it is intended that the magazine 38 will be removed from the sampling device 28 after the magazine 38 has been filled. The removed magazine 38 can then be replaced on the sampling device 28 by another, similar magazine 38. In order to identify a specific magazine 38 during downstream processing, each magazine 38 is provided with a distinct feature 39 such as a barcode or RFID.

Figure 4:
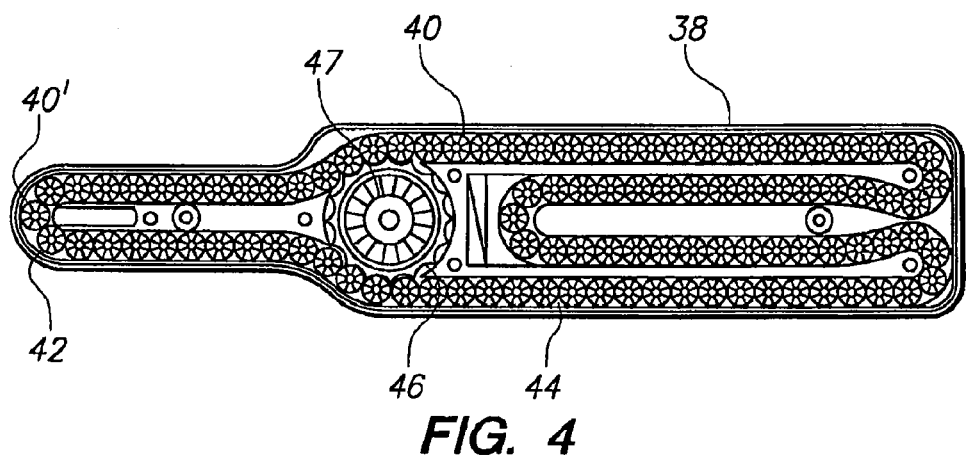
FIG. 4 is a top view of a magazine used for the present invention.

FIG. 4 shows that in certain embodiments the magazine 38 includes ninety-nine storage locations 40 for collecting plant material (e.g., leaf plugs). In the embodiment shown, the storage locations 40 are capsules that are positioned in the magazine 38, along with a register 42, on a pathway 44. One or more leaf plugs can be collected in a single storage location 40. While capsules 40 are illustrated, it is envisioned that the magazine 38 could employ a variety of storage locations 40, such as other types of containers or areas which hold plant samples via adhesion or other attractive forces. As shown, the capsules 40 are conveyed along the pathway 44 by a drive mechanism 46 that is mounted on the magazine 38, as shown. The sampling device 28, in turn, operates the drive mechanism 46. Thus, by using the register 42 as a starting point, the sampling device 28 is able to align the capsules 40 in an ordered sequence along the pathway 44. The capsules 40 are thereby sequentially presented, in order, as individual capsules 40 at a punch position (shown in FIG. 4 as the position of capsule 40'). Further, the sampling device 28 includes a counter 47 for determining the position of each capsule 40 relative to the register 42. In FIG. 4, it is noted that the capsules 40 are limited to movement on the pathway 44. Further, the illustrated drive mechanism 46 rotates to sequentially engage certain capsules 40 to impart movement to all the capsules 40 along the pathway 44. While these structures cooperate to collect plant samples at the punch position 40', other systems and structures are contemplated for sequentially conveying storage locations 40 along the pathway 44. In other embodiments, the magazine 38 includes 100 storage locations 40 for collecting plant material.

It is at the punch position (shown in FIG. 4 by capsule 40') that the punch 32 creates a leaf plug. When a capsule 40 has been filled with the desired number of leaf plugs (e.g., up to eight leaf plugs), the drive mechanism 46 moves the next-in-line capsule 40 into the punch position. Once the capsules 40 of the magazine 38 have been appropriately filled, the magazine 38 is removed from the sampling device 28. The magazine 38 and its contents (i.e., capsules 40 filled with leaf plugs) may be freeze-dried or otherwise preserved. Next, the freeze-dried magazine 38 is bundled with other magazines 38 and prepared for further processing.

Returning to FIG. 1, it is again noted that during the collection of samples from plants 20, each plant 20 being sampled is first identified by its unique feature 22. Further, it will be appreciated that the sampling data obtained by the sampling device 28 for a magazine 38 is sent to the controller 12 via the handheld computer 31. Specifically, this sampling data will allow the contents (i.e., plant material) of a particular storage location 40 in each magazine 38 to correspond with information on the unique feature 22 of the plant 20 from which the plant material was taken. Stated differently, each storage location 40 is identified with a particular unique feature 22 and with the corresponding plant identity in the database 14. Thus, the work-list 26 that is collated by the controller 12 will include information about the location and the identity of the plant 20 that provided the plant material being held at a particular storage location 40 as well as the identity of the magazine 38 and the storage location 40 in the magazine 38 that holds the plant material. The work-list 26 and the magazine 38 are then both used in a transfer process at the transfer station 50 in FIG. 1.

Figure 5:
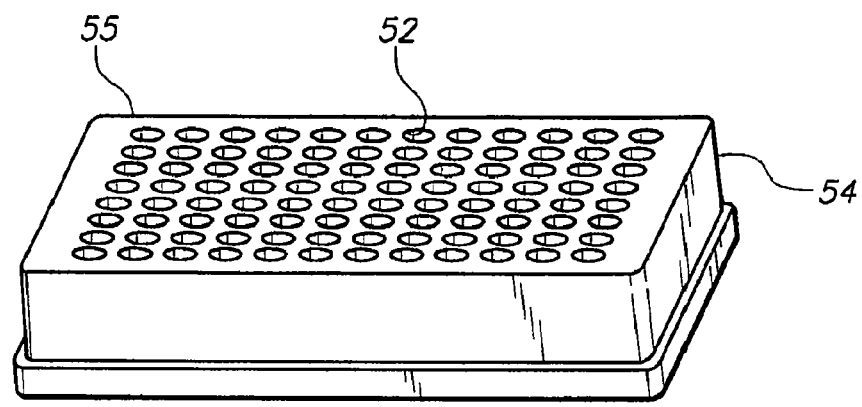
FIG. 5 is a perspective view of a tray used in processing plant samples.
Figure 6:
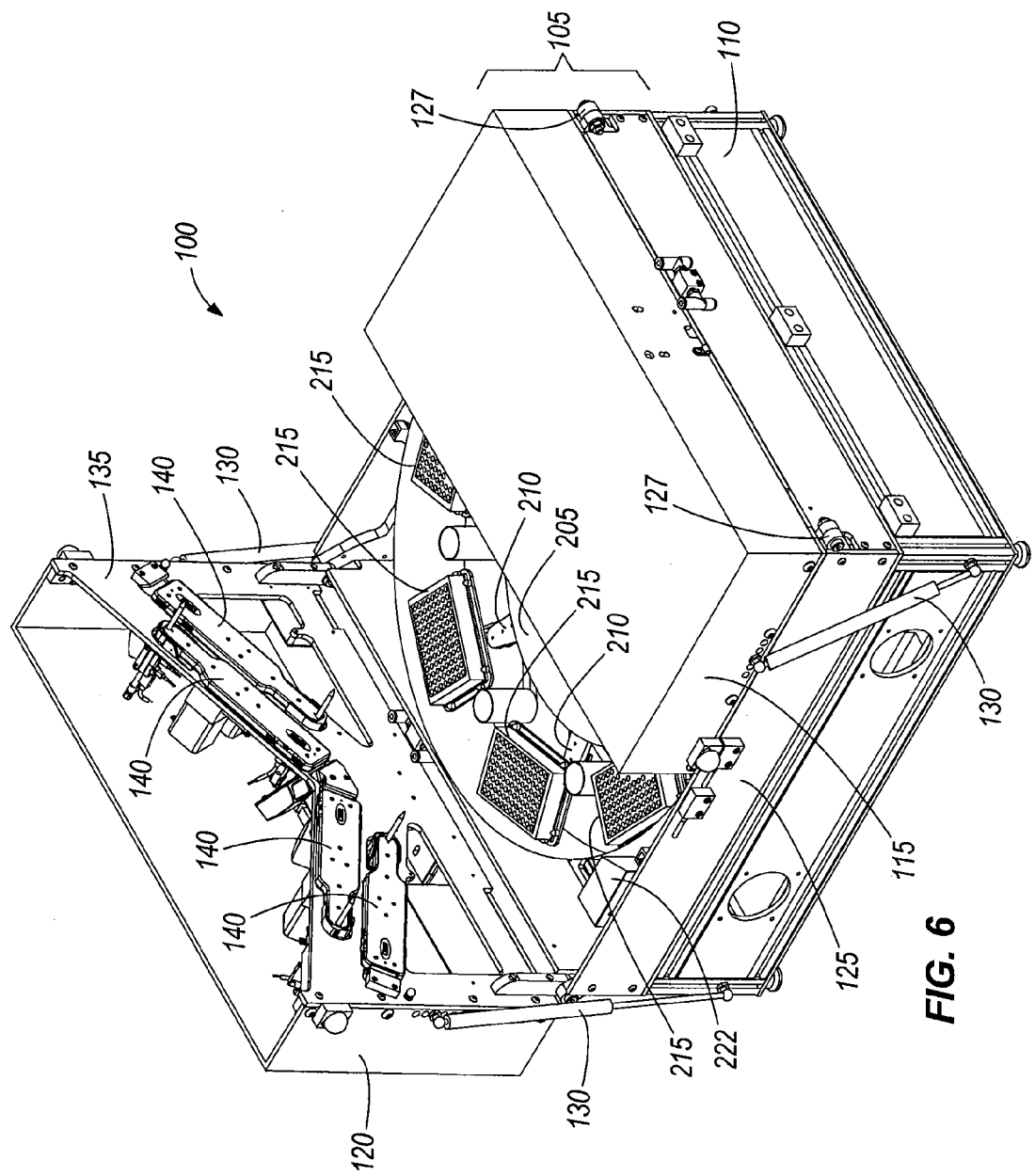
FIG. 6 is a perspective view of a transfer station in accordance with the present invention.
Figure 7:
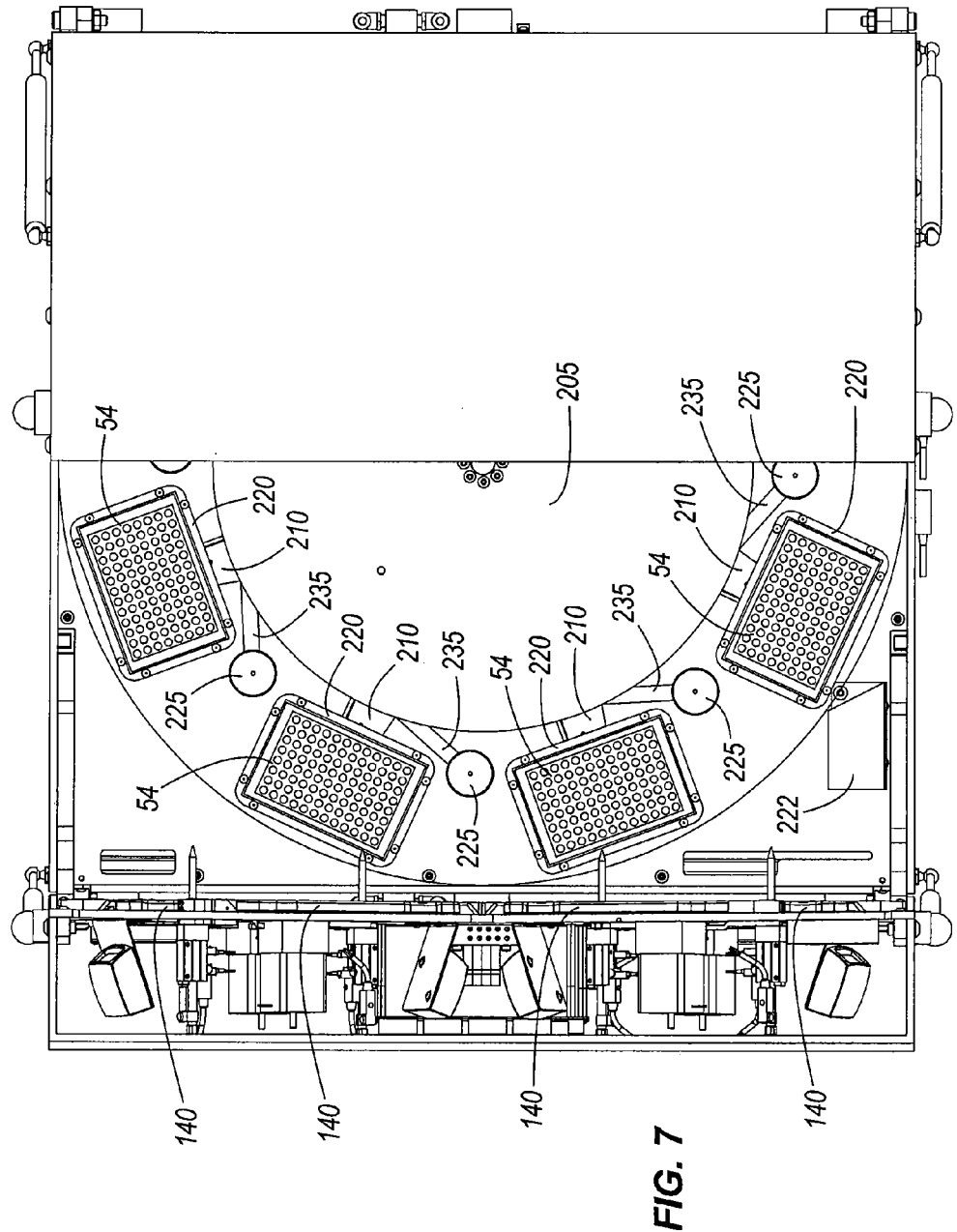
FIG. 7 is a top view of the transfer station of FIG. 6.
Figure 8:
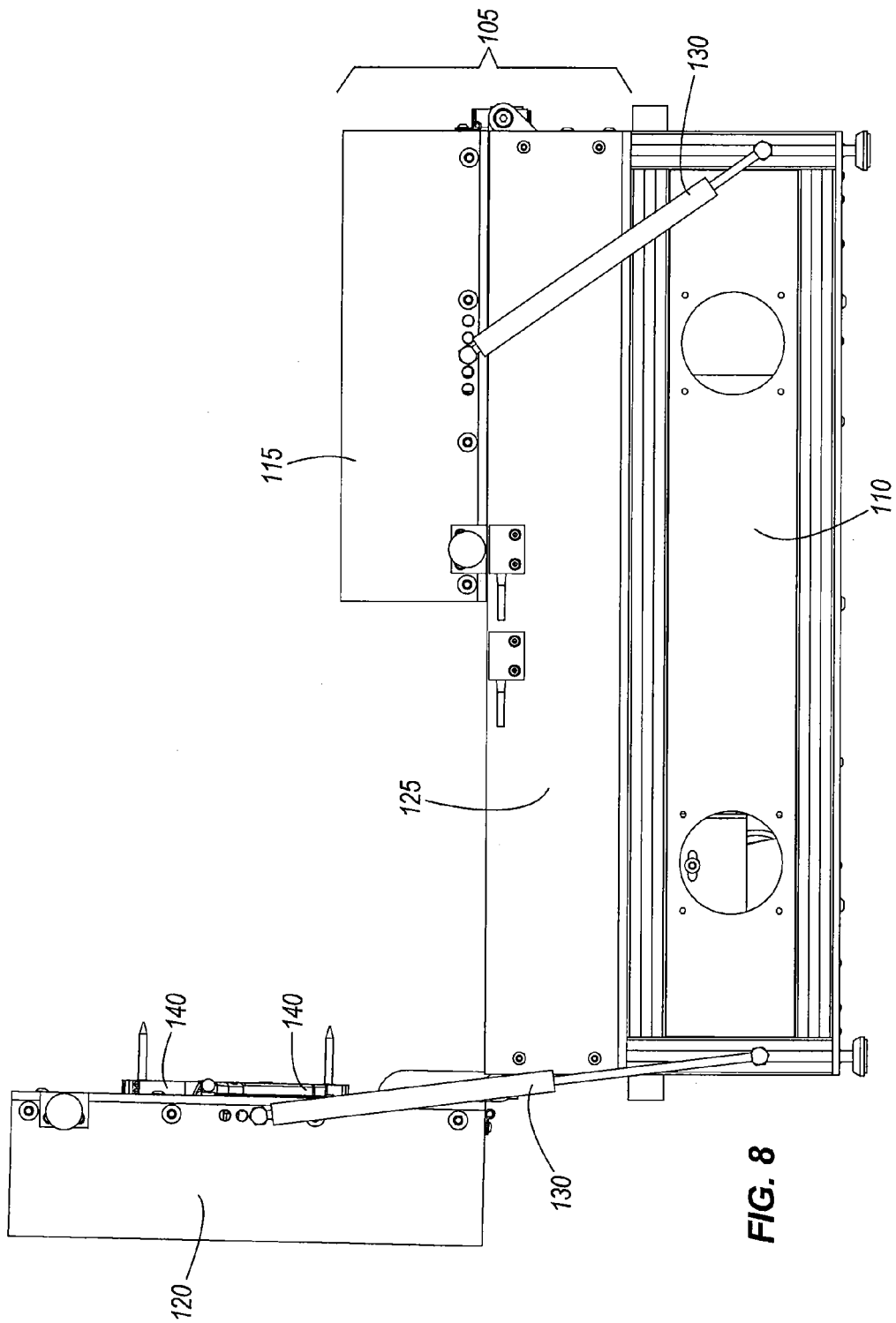
FIG. 8 is a side view of the transfer station of FIG. 6.
Figure 9:
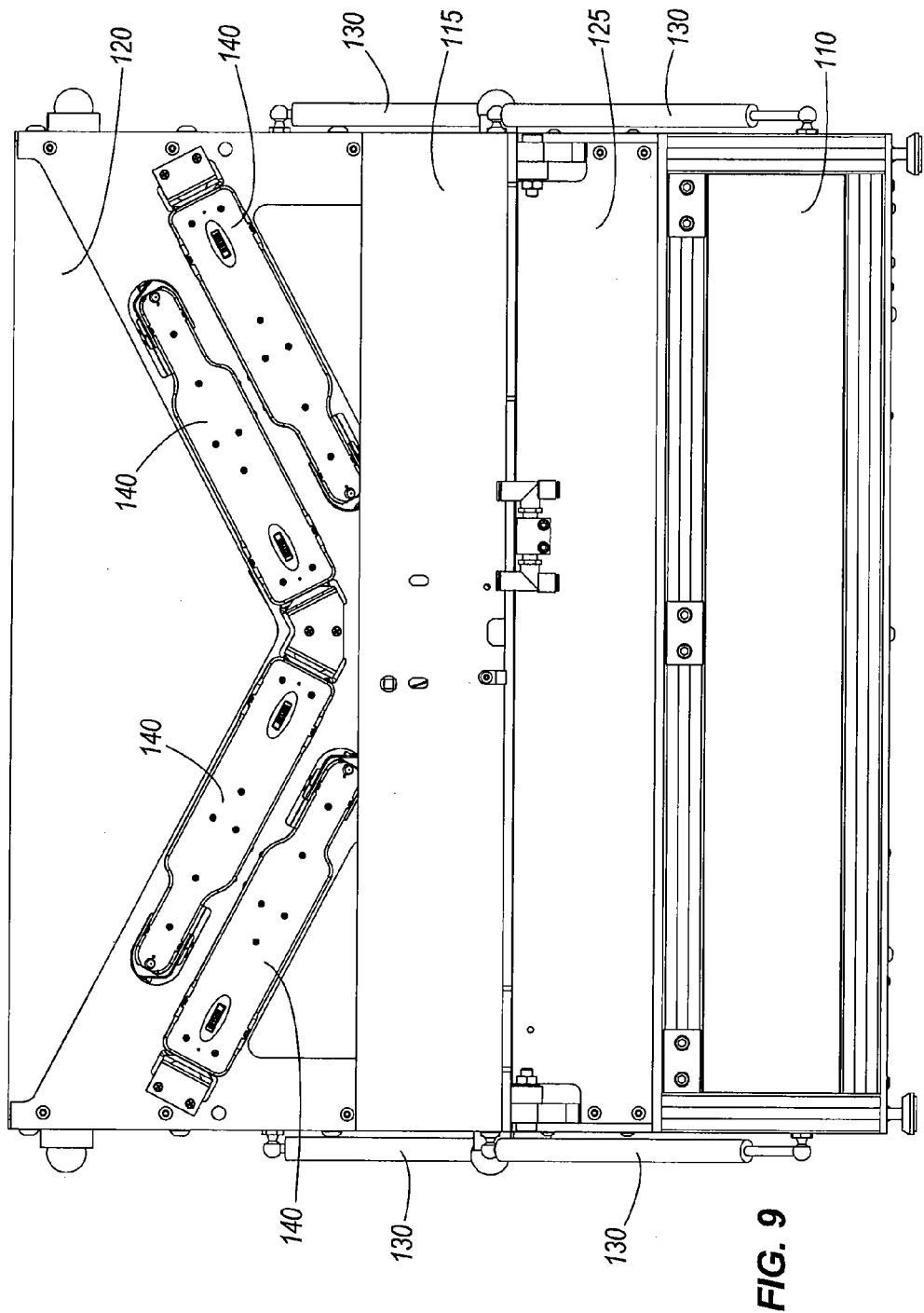
FIG. 9 is front view of the transfer station of FIG. 6.
Figure 10:
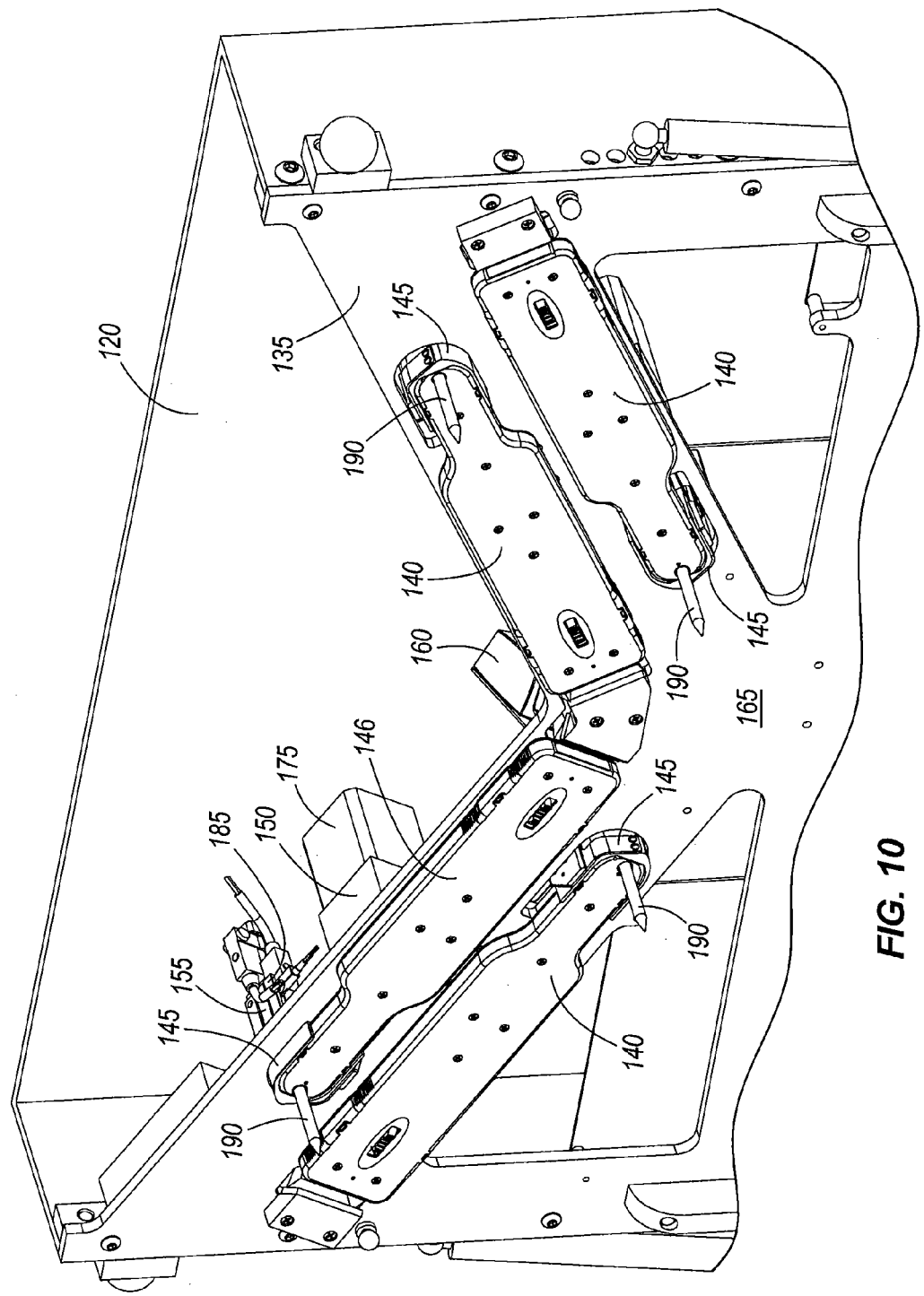
FIG. 10 is a perspective view of a portion of the transfer station of FIG. 6.
Figure 11:
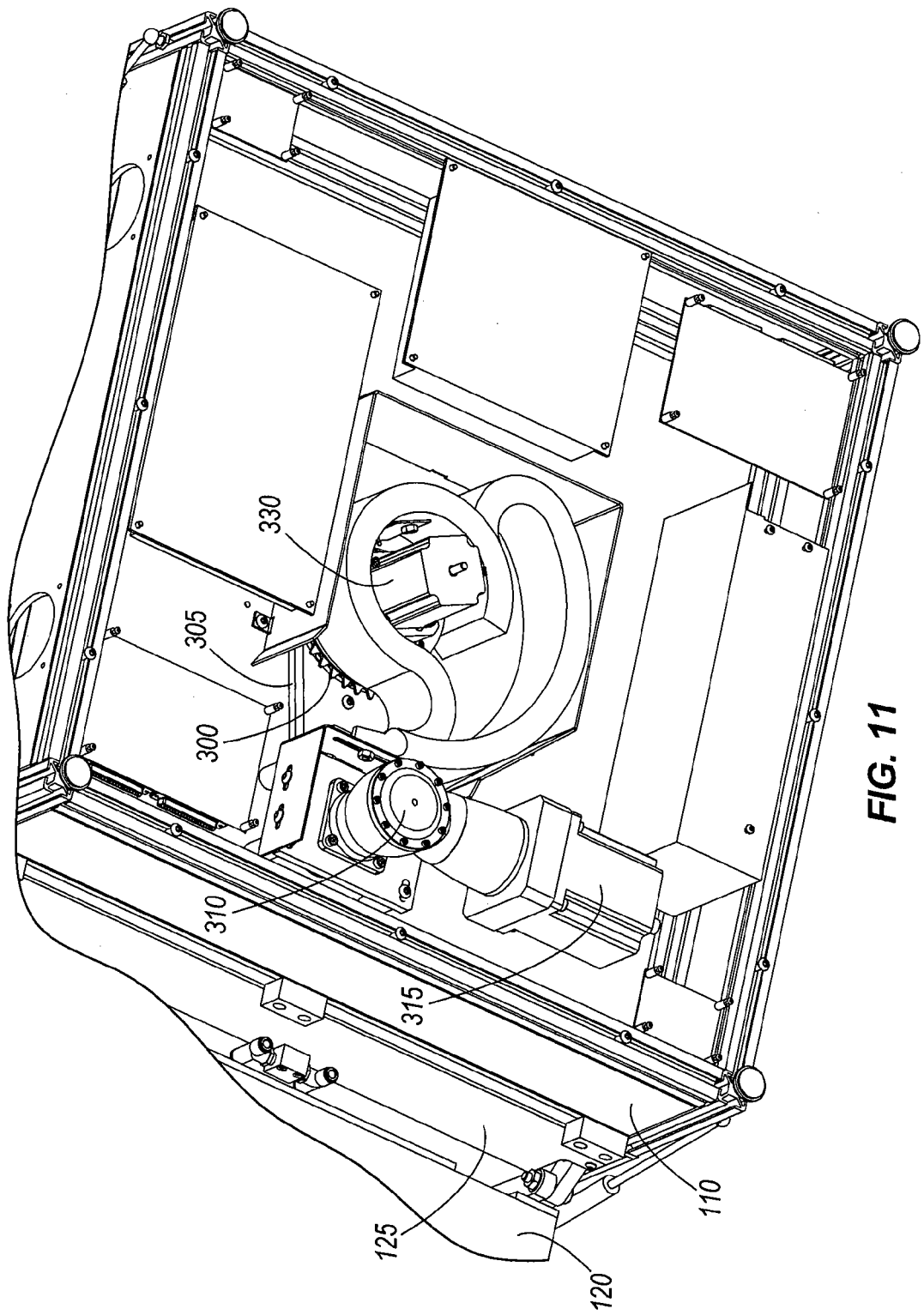
FIG. 11 is a bottom perspective view of the transfer station of FIG. 6.

In simple terms, the transfer process carried out at the transfer station involves the transfer of plant material from individual storage locations 40 of a magazine 38 into respective wells 52 of a receiving member 54 (such as a micro-titre tray or plate). As seen in FIG. 5, the receiving member 54 that is used for the transfer is a tray and includes a plurality of wells 52 (e.g., ninety six wells). The wells 52 are typically arranged in a rectangular array with labeled rows and columns. Further, one corner of the tray 54 is typically identified as the origin so that the wells 52 on the tray 54 can be distinguished from one another. In certain embodiments, the tray 54 includes a discrete feature 55 which allows the identification of each specific well 52. Specifically, the feature 55 allows identification of the receiving member 54 and the origin and arrangement of the wells 52 serve as a key for determining the location of a particular well 52 on the receiving member 54.

Example of Plant Material Sampling

In order to further explain the system 10, an example of plant-material sampling is provided. In the example, an experiment (labeled EXAM) is planned for analyzing certain genetic features in the progeny of two plants. It is determined that the experiment requires samples from one hundred plants, including ten from each parent and eighty from the progeny. Therefore, a database 14 is created with virtual identifications for plants labeled EXAM-001 through EXAM-100. Further, the database 14 is structured so that the parent plants be numbered EXAM-081 through EXAM-100.

In order to ensure that a sufficient number of progeny are grown, one hundred and fifty progeny seeds are planted. During planting, the seeds are located in six rows of twenty-five. Also, each pair of ten genetically-identical parent plants is planted in two defined rows. After the progeny seeds sprout into viable plants, the plant labeling process takes place. Specifically, beginning at a known location relative to the plants 20 (for instance, the north east corner of the array of plants 20), a user attaches a unique feature 22 to every fifth plant. The user follows a set pattern, such as north-to-south through each row and east-to-west from row to row. Once sufficient unique features or identifiers 22 for eighty progeny and twenty parent plants have been applied, the labeling process is finished. With the completion of the labeling process, each plant 20 to be tested has been matched with one of the virtual identifications in the database 14. Of course, a unique feature 22 could be attached to every plant or at a ratio different than once every five plants.

Thereafter, plant samples may be taken from the plants 20. Specifically, the user uses the plant sampling device 28 to read the distinct feature or identifier 39 on a magazine 38, and then connects the magazine 38 to the sampling device 28. The sampling device 28 automatically locates the register 42 within the magazine 38 and is prepared to insert a plant sample at the first storage location 40. Thereafter, the user identifies the first plant 20, by using the sampling device 28 to read the unique feature 22 at the plant 20. Then, the user operates the keypad 36 on the sampling device 28 to take from the plant 20 the desired number of samples. After the desired samples from the first plant 20 have been taken, the user instructs the sampling device 28 that the adjacent plant 20 will be sampled. This process is repeated until the next plant 20 having a unique feature 22 is encountered. Then the sampling device 28 is used to read the unique feature 22, as was done with the first plant 20.

As the unique features 22 are read, the user ensures that the number of plants 20 believed to be sampled and the actual number of samples taken according to the sampling device 28 are the same. For instance, in this example, when using the plant sampling device 28 to read the unique feature 22 at the sixteenth plant, the user notices that the plant sampling device 28 has already recorded taking sixteen samples. Because sampling at the eleventh plant did not display this error, the user knows that a mistake was made between the eleventh and sixteenth plants 20. In order to correct the error, the user enters a mistake code into the plant sampling device 28 and returns to the eleventh plant. The unique feature 22 at the eleventh plant is read and a sample is taken. Then, the user proceeds with the typical sampling process.

When a desired number of samples or the maximum number of samples have been received in the magazine 38, the user disconnects that magazine 38, reads the distinct feature 39 from a replacement magazine 38 and connects the replacement magazine 38 to the plant sampling device 28. Again, the sampling device 28 automatically finds the register 42 within the magazine 38 and positions the first storage location 40 to receive a sample.

When the sampling process is finished, the magazines 38 are carried or otherwise transported to a transfer station 50. Also, the sampling data is communicated to the controller 12 by the handheld computer 31. At the transfer station 50, the work-list 26 is read and the transfer instructions are performed. For instance, the work-list 26 may require that one sample from each parent plant and ten samples from the progeny be positioned in specific wells 52 on ten trays 54. Thereafter, each magazine 38 is sequentially identified and connected to the transfer station 50. Further, each tray 54 is connected to the transfer station 50 and is identified by the transfer station 50. For each magazine 38, the controller 12 identifies the source plant 20 for the sample at each storage location 40 based on the data received from the handheld computer 31. According to the work-list 26, the transfer station 50 transfers each sample to a selected well 52 in a selected tray 54. Thereafter, the plant source for any sample can be identified by identifying the well 52 and tray 54 in which the sample is located. With the well 52 and tray 54 known, the storage location 40 and magazine 38 are known, thus the plant 20 from which the sample came is known. As noted above, the controller 12 has identified the storage locations 40 that include sampling mistakes. Therefore, those storage locations 40 are not transferred to the trays 54

Transfer Station

As shown in FIGS. 6-9, the transfer station 50 includes a housing 105 that is supported on a stand 110. Two upper housing portions 115, 120 are pivotally connected to a housing base 125 by hinges 127. A pair of struts 130 connect each upper housing portion 115, 120 to the stand 110. The struts 130 hold each of the upper portions 115, 120 in an open position. In a closed position, each upper portion 115, 220 is substantially horizontal. Each of the upper housing portions 115, 120 is identical. Therefore, only one of the upper housing portions will be described in detail.

As shown in FIGS. 10-14, the upper housing portion 120 includes a platform 135 mounted at a lower end of the upper housing portion 120. Four sample removal stations or magazine positions 140 are mounted on the platform 135. Each sample removal station 140 includes a magazine receiver 145, a magazine indexer 150, a punching rod assembly 155, and a barcode scanner 160. The magazine receiver 145 is mounted on a bottom surface 165 of the platform 135 and is configured to receive and secure a magazine 38. The magazine receiver 145 includes a latch that engages a portion of the magazine 38 to secure the magazine to the magazine receiver 145. The magazine indexer 150 is mounted on a top surface 170 of the platform 135. The magazine indexer 150 includes a motor 175 and a shaft 180 that extends through the platform 135 to engage the drive mechanism 46 of the magazine 38. The punching rod assembly 155 is mounted to the top surface 170 of the platform 135.

The punching rod assembly 155 includes an actuator 185 and a punching rod 190. The punching rod 190 is concentrically aligned with an aperture through the platform 135 that allows the punching rod 190 to move to a removal position where at least a portion of the punching rod 190 extends through the aperture and past the magazine 38. The punching rod 190 is cylindrical. The actuator 185 drives the punching rod 190 between a retracted position in which the punching rod 190 does not extend past the bottom surface 165 of the platform 135 and the punching position.

Figure 14:
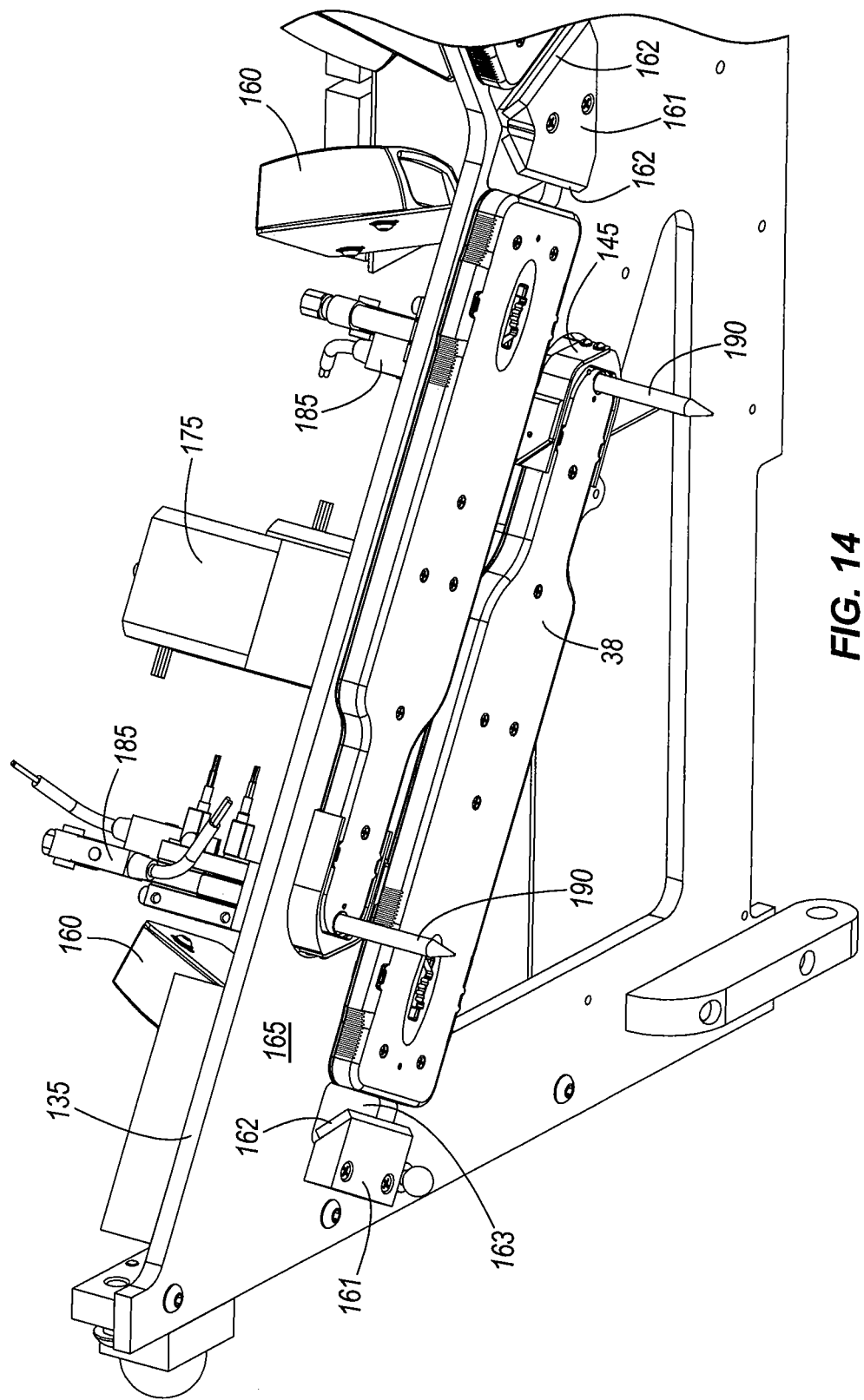
FIG. 14 is a perspective view of a portion of the transfer station of FIG. 6.

As shown in FIG. 14, the barcode scanner 160 is mounted to the top surface 170 of the platform 135 and is configured to read the barcode 39 of the magazine 38. The barcode scanner 160 is mounted near an aperture 163 through the platform 135. A block 161 is mounted on the bottom surface 165 near the aperture 163. A mirror 162 is mounted on the block 161 such that a laser emitted by the barcode reader 160 is redirected by the mirror 162 to read the barcode 39 located on the end of the magazine 38.

As shown in FIGS. 7 and 16-18, a carousel 195 is positioned at least partially within the housing base 125. The carousel 195 includes a wheel 200 and a plate 205. The wheel 200 includes eight spokes 210. A sample receiving station or tray position 215 is positioned at a distal end of each of the eight spokes 210. The sample receiving station 215 includes a tray receiver 220 and a linear positioning slide 230. A waste collector 225 is mounted to a support arm 235 that extends from each spoke 210. The waste collector 225 is an open-topped cylinder configured to receive unwanted samples or error samples. A single barcode scanner 222 is positioned near the carousel 195 such that the barcode 55 on each tray 54 can be scanned by the barcode scanner 222 by rotating the carousel 195 such that the tray 54 passes by the barcode scanner 222.

The tray receiver 220 is configured to receive and secure a tray 54. The tray receiver 220 includes eight positioning projections 240 arranged in pairs of two, such that each pair engages a corner of the tray 54. The tray receiver 220 is mounted to an upper portion 245 of a support bracket 250. The upper portion 245 is positioned above a top surface 255 of the spoke 210. The support bracket 250 includes an arm 260 having a cam roller 265. The cam roller 265 is positioned above the top surface 255 of the spoke 210. A lower portion 270 of the support bracket 250 is connected to a movable portion 275 of the linear positioning slide 230. The linear positioning slide 230 is mounted on a bottom surface 280 of the spoke 210. The movable portion 275 is connected to the linear positioning slide 230 such that the movable portion 275 can travel along the length of the linear positioning slide 230. The linear positioning slide 230 is aligned with a radius of the wheel 200 such that the movable portion 275 travels radially with respect to a centerpoint 285 of the wheel 200. An axis of rotation extends through centerpoint 285 of the wheel and is normal to the top surface 255. The cam roller 265 engages at least one surface of a groove 290 formed in a bottom surface 295 of the plate 205.

As shown in FIGS. 11 and 16-18, a sprocket 300 is mounted to the carousel 195. The sprocket 300 is centered on the axis of rotation. A drive belt 305 connects the sprocket 300 to a gear box 310. The gear box 310 is connected to a carousel motor 315 such that the carousel motor 315 drives the gear box 310, which rotates the sprocket 300 via the drive belt 305, thereby rotating the carousel 195 about the axis of rotation. A bearing 320 is mounted to the stand 110, supports the carousel 195, and is centered on the axis of rotation.

The plate 205 is positioned above the wheel 200. The plate 205 is concentric with the wheel 200. A shaft 325 extending through the carousel 195 connects the plate 205 with a plate motor 330. The plate motor 330 rotates the shaft 325, which in turn rotates the plate 205. The plate motor 330 is mounted to the carousel 195 such that the plate motor 330 rotates with the carousel 195. The plate 205 can be rotated independent from the wheel 200. A plurality of grooves 290 extend from the bottom surface 295 of the plate 205 into the plate 205 and receive the cam rollers 265.

Figure 17:
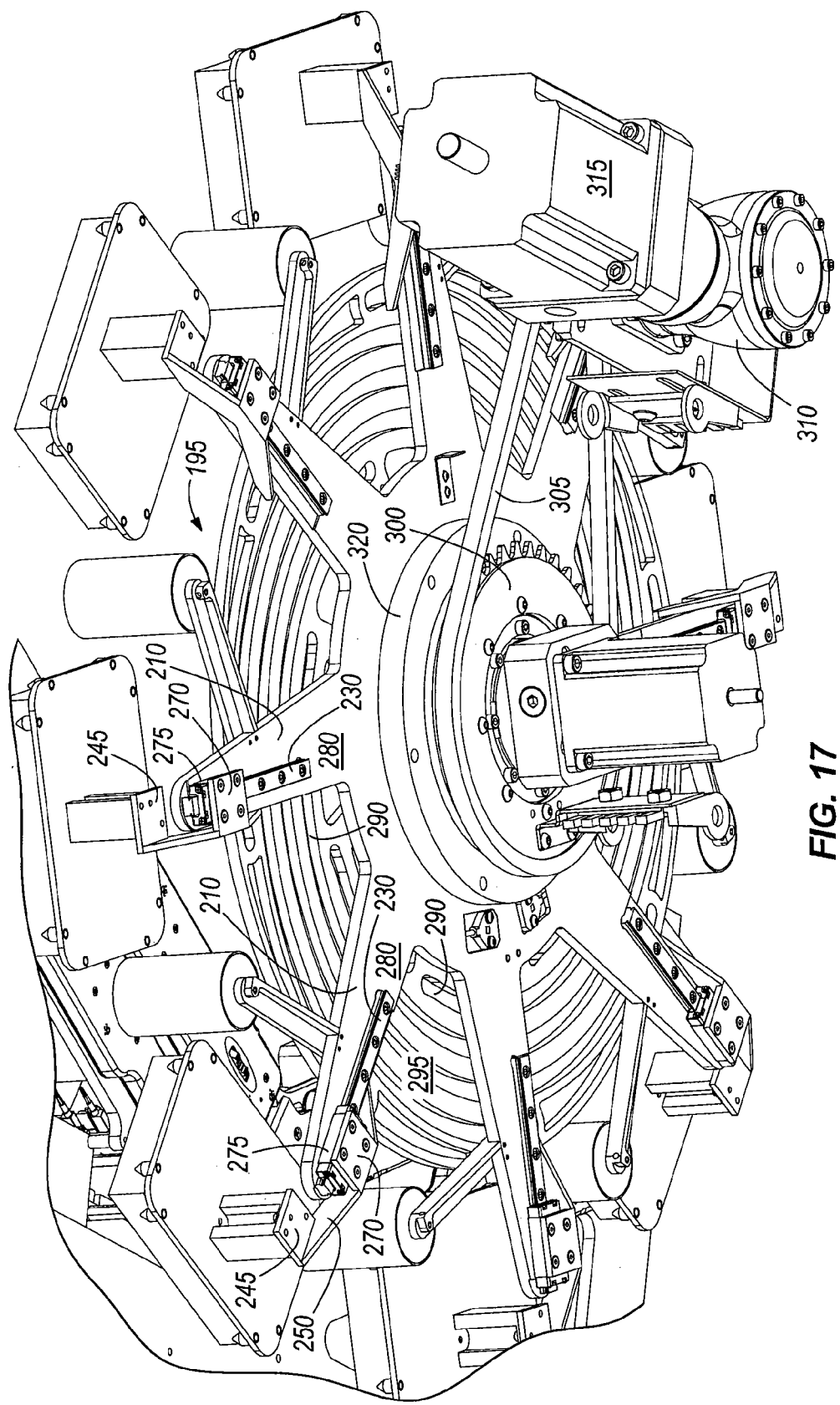
FIG. 17 is a perspective view of a portion of the transfer station of FIG. 6.
Figure 18:
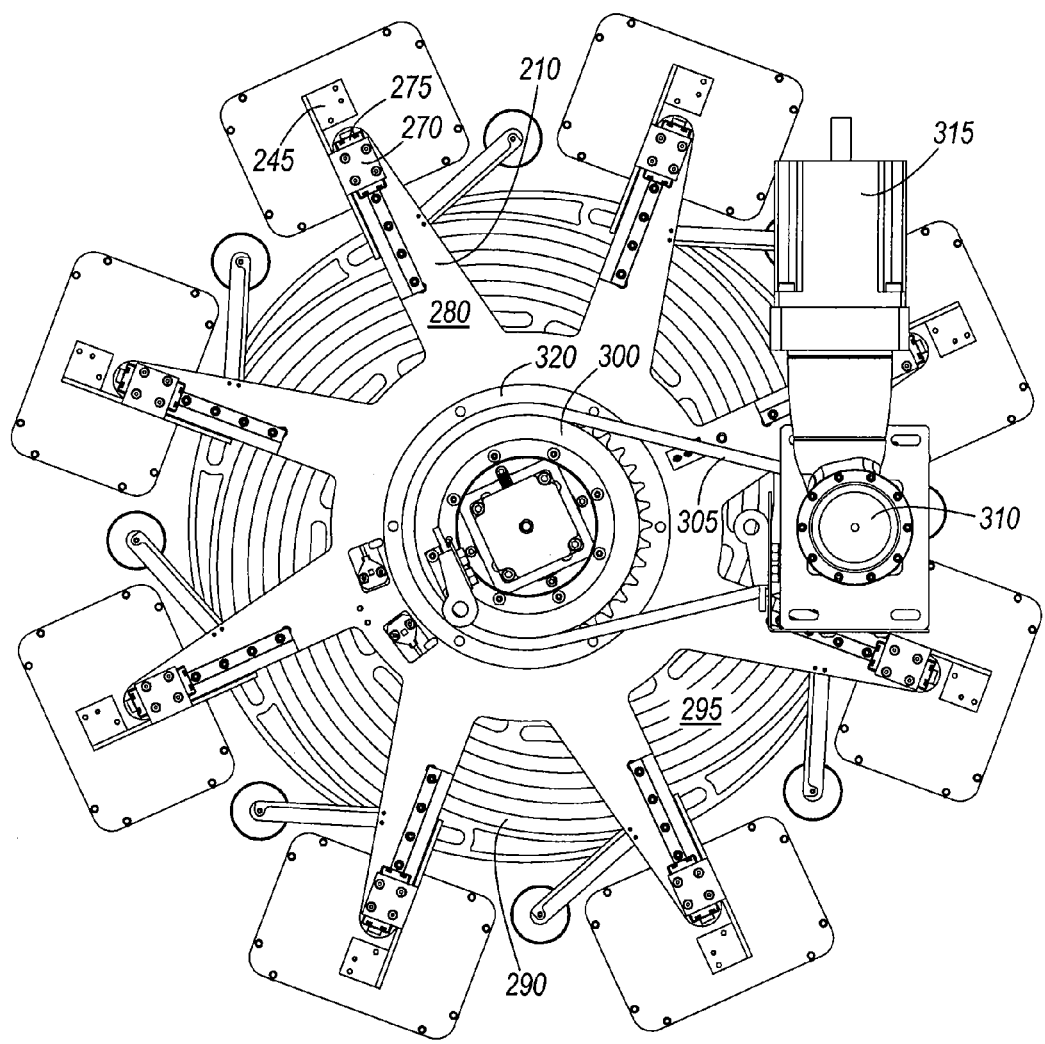
FIG. 18 is a bottom view of a portion of the transfer station of FIG. 6.
Figure 19:
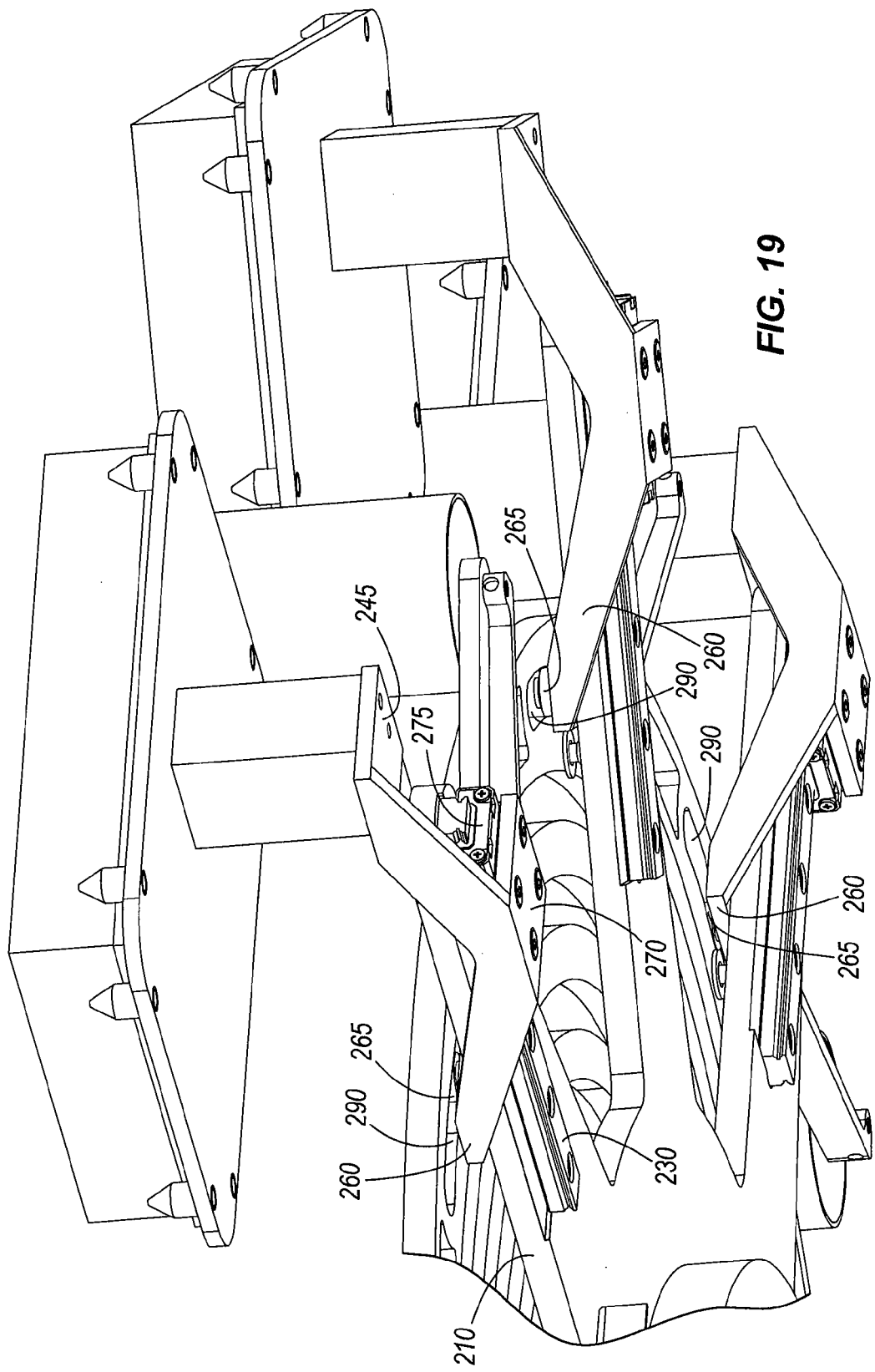
FIG. 19 is a perspective view of a portion of the transfer station of FIG. 6.

As shown in FIGS. 17-19, the tray receiver 220 moves tangentially with respect to the centerpoint 285 of the wheel 200 as the wheel 200 rotates. The tray receiver 220 moves radially with respect to the centerpoint 285 of the wheel 200 along the linear positioning slide 230. To move the tray receiver 220 radially, the plate motor 330 rotates the plate 205. As the plate 205 rotates, one of the plurality of grooves 290 in the bottom of the plate 205 engages the cam roller 265 of the support bracket 250 and causes the support bracket 250 and the movable portion 275 to move radially along the linear positioning slide 230. Because all of the cam rollers 265 are engaged by a groove 290 in the plate 295, when the plate 295 rotates all of the tray receivers 220 are moved to the same radial position on their respective linear positioning slides 230. Alternatively, each of the tray receivers 220 could be individually radially moved by using a motor assembly to move the respective movable portion 275 along the respective linear positioning slide 230.

Figure 12:
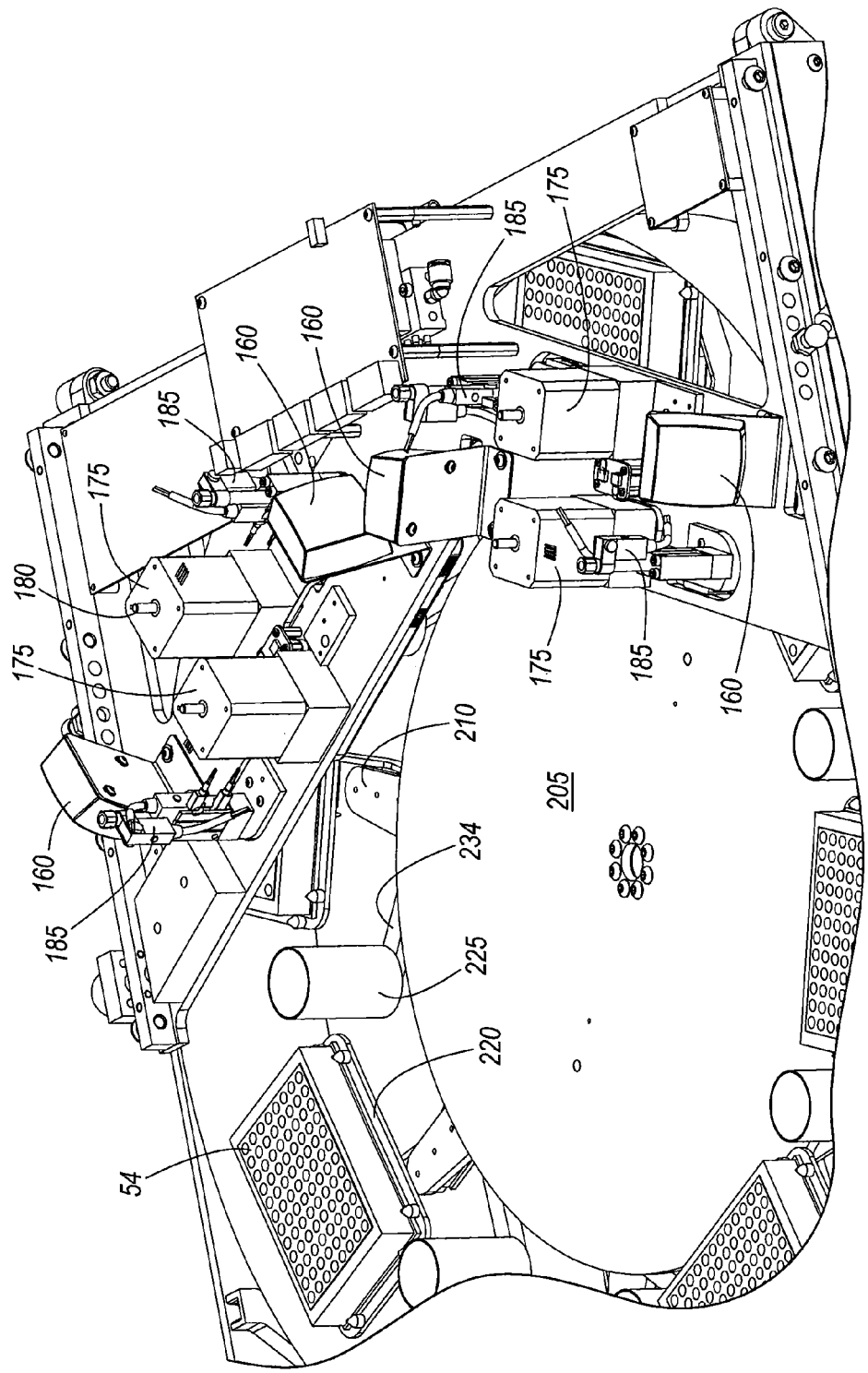
FIG. 12 is a perspective view of a portion of the transfer station of FIG. 6.
Figure 13:
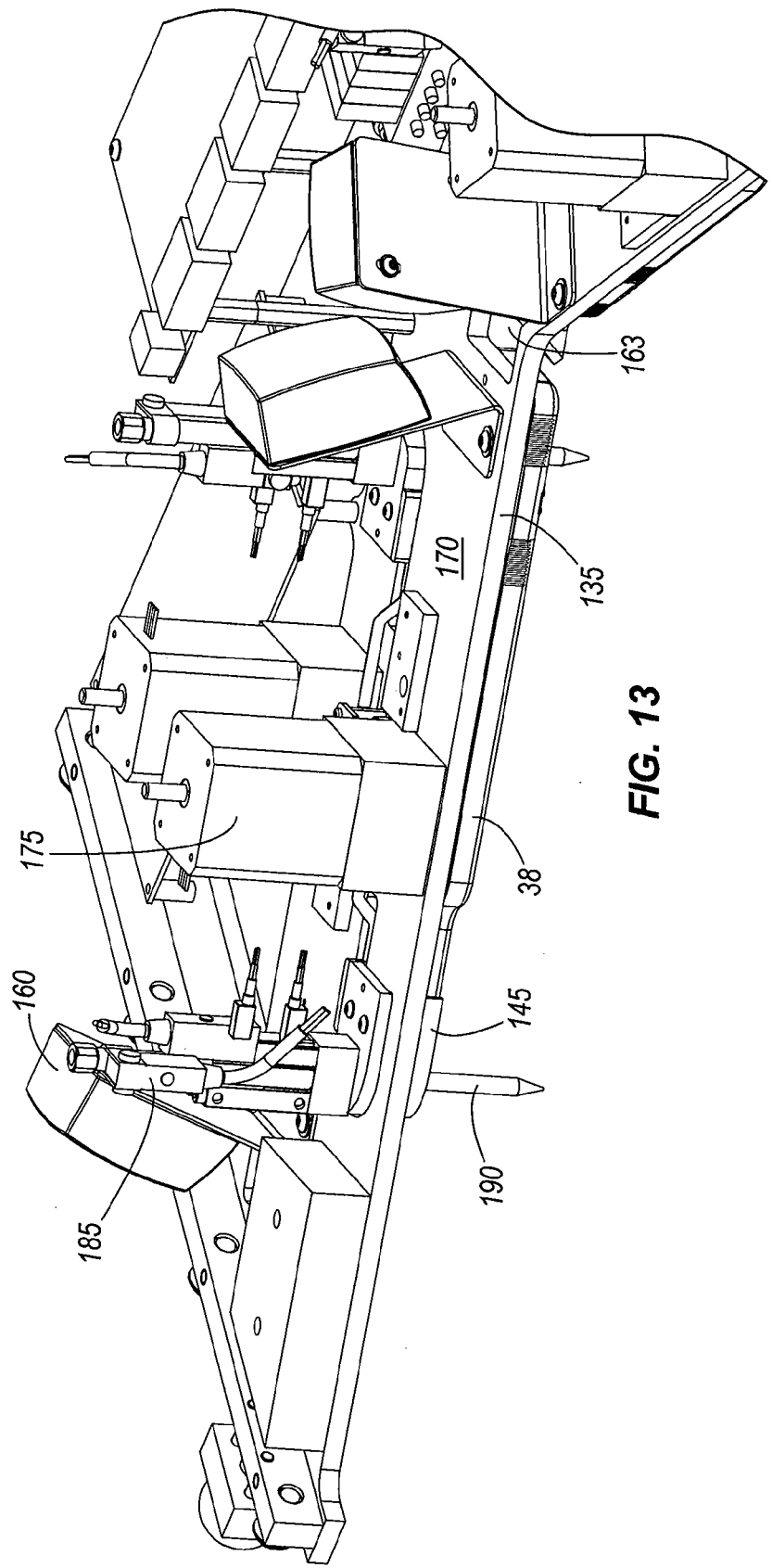
FIG. 13 is a perspective view of a portion of the transfer station of FIG. 6.
Figure 15:
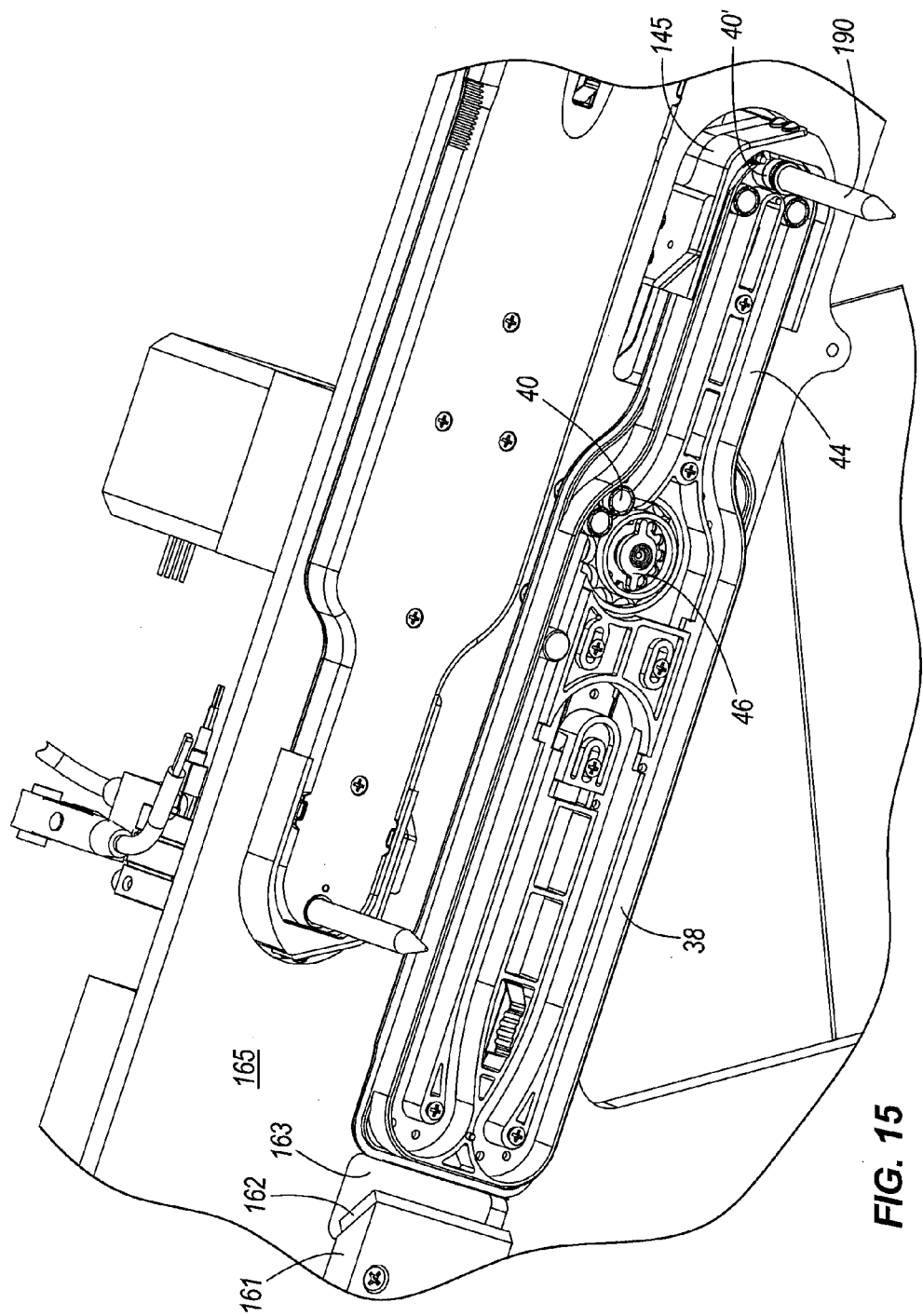
FIG. 15 is a perspective view of a portion of the transfer station of FIG. 6.
Figure 16:
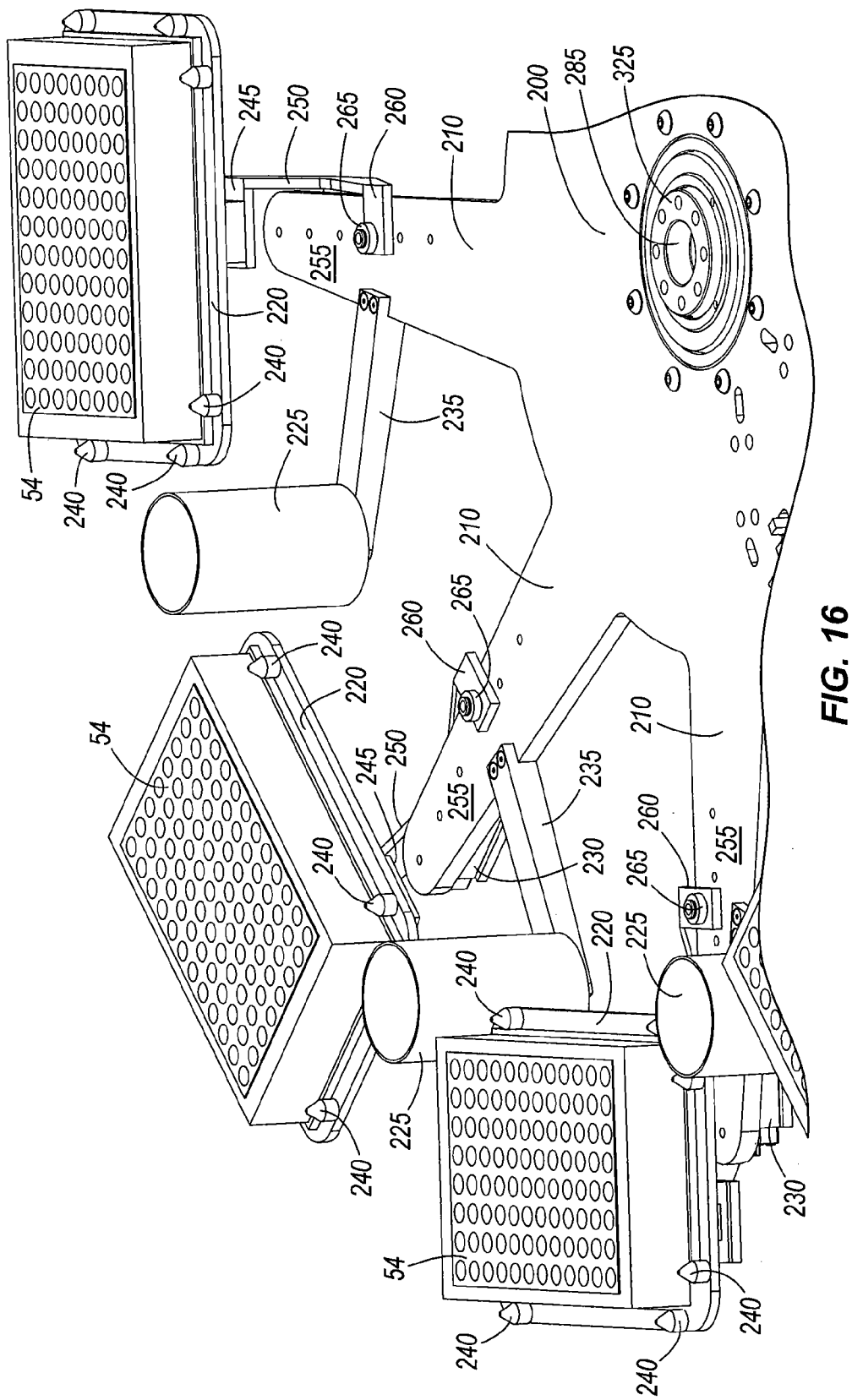
FIG. 16 is a perspective view of a portion of the transfer station of FIG. 6.

As best shown in FIGS. 12 and 17, when both of the upper portions 115, 120 of the housing 105 are in the closed position, each sample removal station 140 is positioned above a sample receiving station 215 such that the position of each magazine 38 is mirrored by the position of each tray 54. As shown in FIG. 15, the punching rod 190 is aligned with a capsule 40 in the punch position 40' of the magazine 38 and with a well 52 in the tray 54 in a target position. The magazine indexer 150 can rotate the drive mechanism 46 so that any of the capsules 40 in the magazine 38 can be located at the punch position 40'. The tray receiver 220 can move so that any of the wells 52 in the tray 54 can be in the target position. The transfer station 50 in the illustrated embodiment includes eight sample removing stations 140 and eight sample receiving stations 215. Of course, the transfer station 50 could include a single sample removing station 140 and a single sample receiving station 215. Also, the transfer station 50 could include fewer than eight sample removing stations 140 and eight sample receiving stations 215 or more than eight sample removing stations 140 and eight sample receiving stations 215.

In use, the capsule 40 with the desired sample is advanced to the punch position 40' of the magazine 38 by the magazine indexer 150 and the drive mechanism 46. The tray receiver 220 is positioned so that the desired well 52 in the tray 54 is in the target position. The actuator 185 advances the punching rod 190 from the retracted position to the removal position, thereby removing the desired sample from the magazine 38 by punching through the magazine 38 and the capsule 40 in the punch position 40'. The punching rod 190 deposits the desired sample in the well 52 in the target position and then returns to the retracted position. After the desired sample is deposited in the well 52 in the target position, the capsules 40 in the magazine 38 are advanced so the next capsule 40 is in the punch position 40', and the tray receiver 220 can be moved so that a different well 52 in the tray 54 is in the target position.

After all wanted samples or non-error samples have been removed from the magazine 38, the unwanted samples or error samples can be transferred from the magazine 38 to the waste container 225 through a clean mode. The first capsule 40 with an error sample is advanced to the punch position 40' of the magazine 38 and the waste container 225 is moved to the target position. In the target position, a centerpoint of the waste container 225 is aligned with the punching rod 190 and the capsule 40 in the punch position 40' of the magazine 38. The actuator 185 advances the punching rod 190 from the retracted position to the removal position, thereby removing the error sample from the magazine 38 by punching through the magazine 38 and the capsule 40 in the punch position 40'. The punching rod 190 deposits the desired sample in the waste container 225 and then returns to the retracted position. This process is repeated for any remaining error samples in the magazine 38. The clean mode can be initiated automatically by the transfer station 50 or initiated by a user. Alternatively, the error samples could be transferred from the magazine 38 to the waste container 225 as they occur in the sequence of capsules 40 in the magazine 38 during the transfer of the wanted samples.

Figure 20:
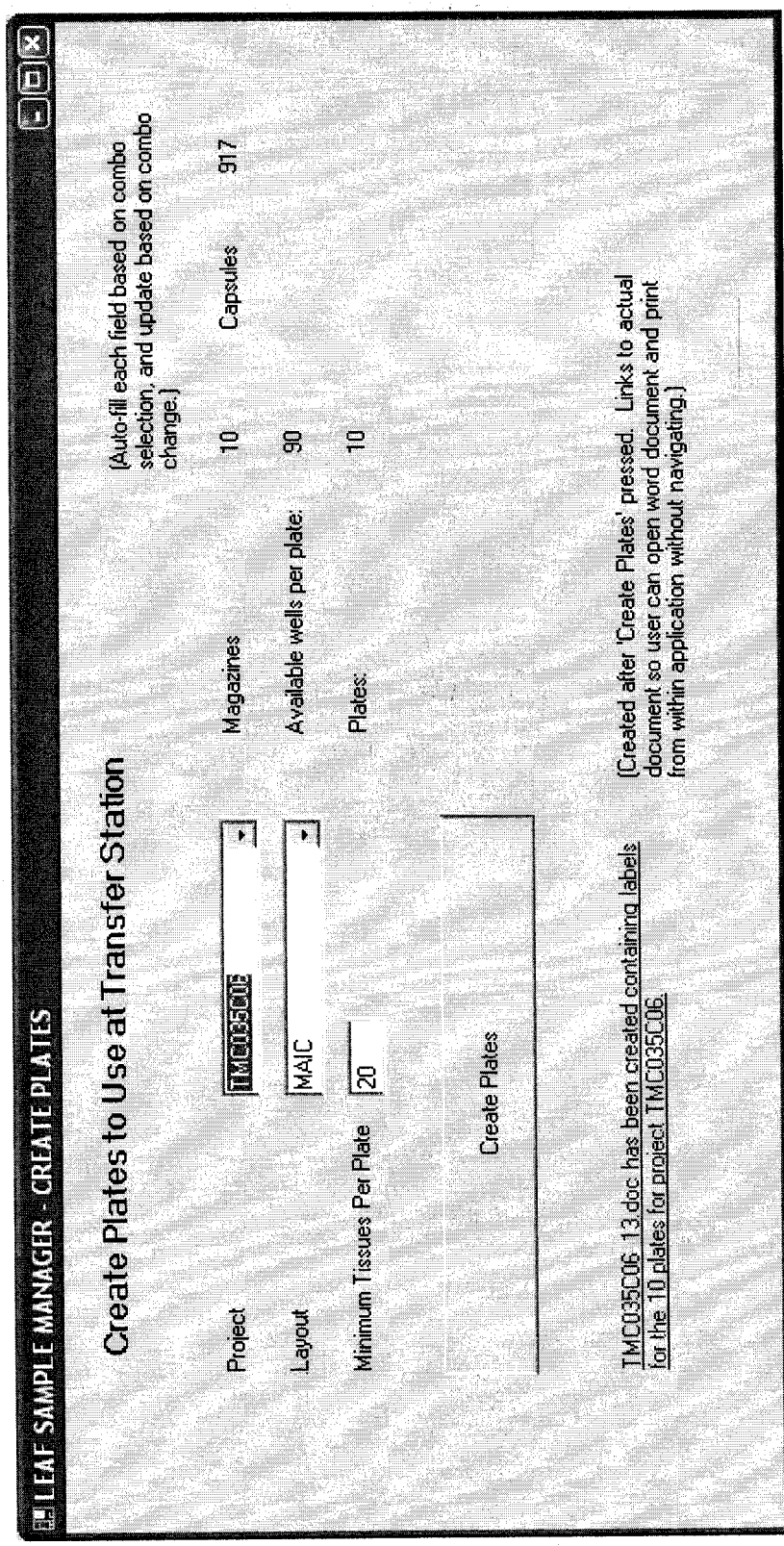
FIG. 20 is a screen shot of a graphical user interface to be used with the transfer station of FIG. 6.

A leaf sample manager is used to create barcodes for the plates or trays 54 and to update the work-list 26. The leaf sample manager includes an input device, a graphical user interface (GUI), and a controller. The input device can be a keyboard, touch screen, barcode scanner, mouse, or other suitable device or combination of devices. FIG. 20 illustrates a "Create Plates" screen 350 as would be displayed on the GUI to enable the user to designate the appropriate project, the layout of the plate, and the minimum number of tissues or samples per plate and a create barcodes for the plates.

Figure 21:
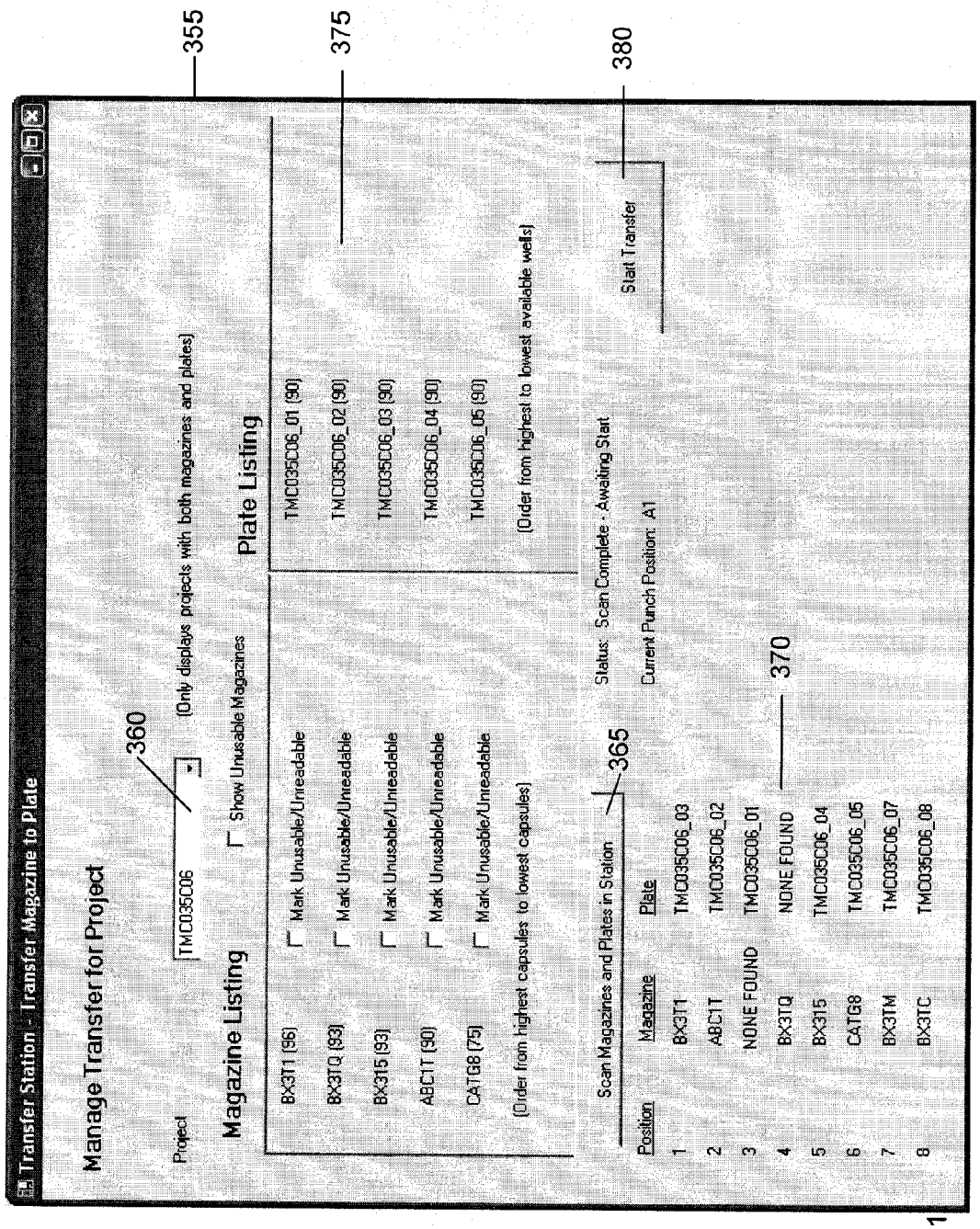
FIG. 21 is a screen shot of a graphical user interface to be used with the transfer station of FIG. 6.

A user interface including an input device, a graphical user interface (GUI), and a controller is configured to allow a user to control the transfer station 50. The input device can be a keyboard, touch screen, barcode scanner, mouse, or other suitable device or combination of devices. The controller is configured to control and receive information from the components of the transfer station 50. FIG. 21 illustrates a "Transfer Magazine to Plate" screen 355 as would be displayed on the GUI to enable the user to control the operation of the transfer station 50.

In use, the desired work-list 26 is loaded to the controller to direct the transfer cycle of the transfer station 50. The desired-work list 26 or project is then selected from the "Project" drop-down menu 360 with the user interface (as shown in FIG. 21). The desired work-list 26 includes associated samples of plant material contained in a plurality of required magazines 38 identified by their barcodes (or other identifiers) and a plurality of required trays 54 identified by their barcodes (or other identifiers). In some embodiments, multiple work-lists 26 can be loaded to the controller.

Figure 22:
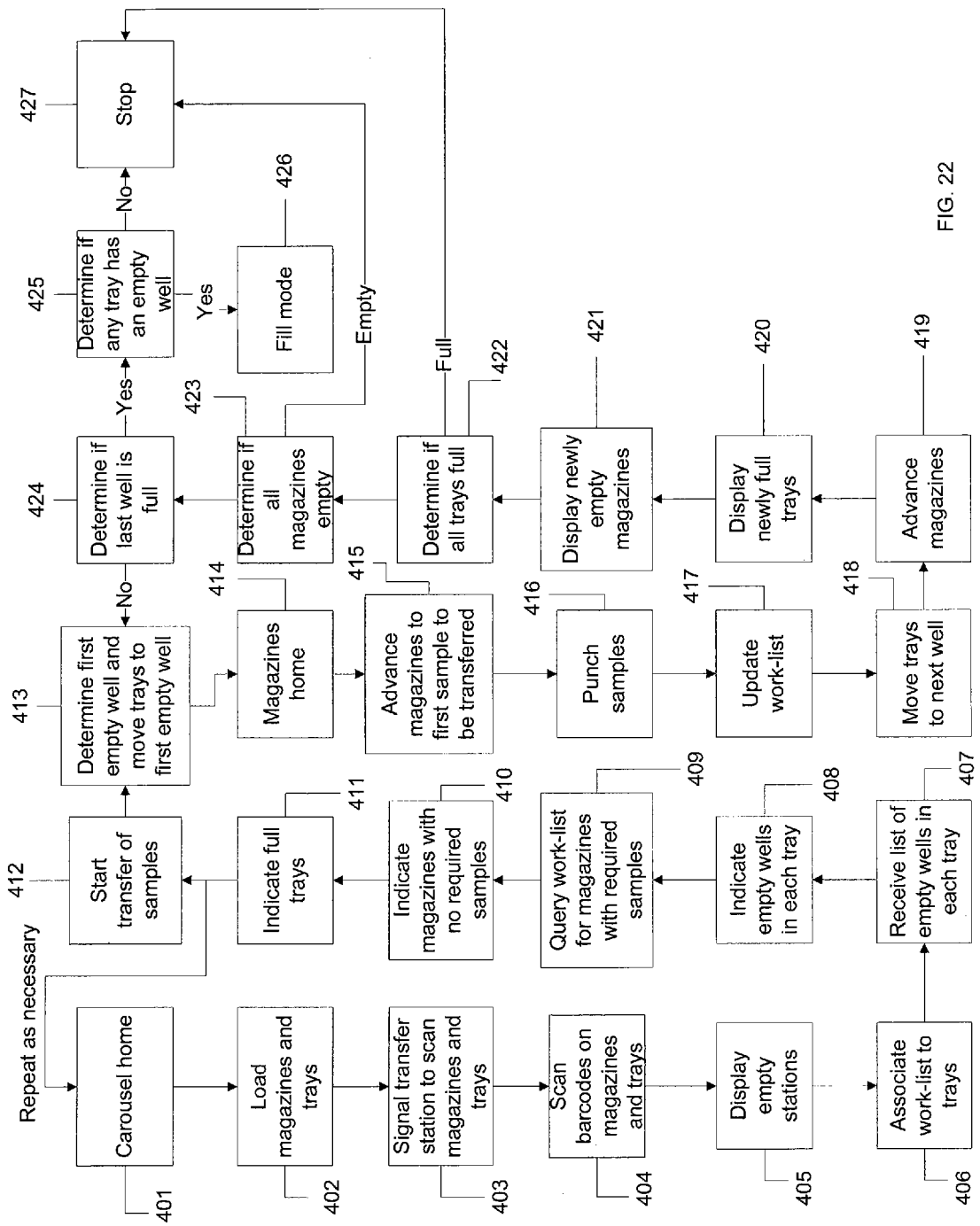
FIG. 22 is a flow-chart describing a process of the transfer station of FIG. 6.

The transfer station 50 cycles through a series of steps illustrated in FIG. 22. In the first step 401, the carousel 195 is rotated to a home position where each sample removal station 140 is positioned above a sample receiving station 215. In the home position, a sample removal station 140 (designated as sample removal station one) is positioned above a sample receiving station 215 (designated as sample receiving station one), and so on, such that all eight sample removal stations are designated as one through eight and all of the corresponding sample receiving stations are also designated as one through eight.

In the second step 402, the user loads the required magazines 38 into the sample removal stations 140 and loads the required trays 54 into the tray receivers 220. After loading the magazines 38 and trays 54, the user closes both of the upper housing portions 115, 120. More magazines 38 than trays 54 can be loaded into the transfer station 50. More trays 54 than magazines 38 can be loaded into the transfer station 50.

In the third step 403, the user interface displays a button 365 (shown in FIG. 21) stating "Scan Magazines and Plates in Station". The user then clicks on that button to move to the fourth step 404.

In the fourth step 404, the barcode 39, 55 on each of the magazines 38 and the trays 54 is scanned. Each barcode scanner 160 scans the barcode 39 of the magazine 38 in each sample removal station 140. When the carousel 195 is in the home position, each tray receiver 220 is in a known position relative to the barcode scanner 222. By rotating the carousel 195 through at least one revolution, the barcode 55 on each tray 54 is scanned by the barcode scanner 222 and associated with the appropriate tray receiver 220. Alternatively, the barcode 55 on each tray 54 can be scanned by a barcode scanner positioned near each tray receiver 220. In other embodiments, a handheld barcode scanner could be used to scan the barcode 39, 55 of each of the magazines 38 and each of the trays 54.

In the fifth step 405, the user interface displays a screen portion 370 (as shown in FIG. 21) showing the empty sample removal stations 140 and empty receiving stations 215, designating the empty stations 140, 215 as "NONE FOUND." A station 140, 215 is determined to be empty if there is no valid barcode scan from the magazine 38 or tray 54 in that station 140, 215. If a station 140, 215 is incorrectly determined to be empty, the user can manually enter the appropriate identifier for the magazine 38 or tray 54 in that station 140, 215. In other embodiments, a sensor configured to detect the presence of a magazine 38 or tray 54 is included for each station 140, 215.

In the sixth step 406, the controller associates the work-list 26 with each of the trays 54. The work-list is associated by tray 54 because trays 54 are associated with a single work-list 26, whereas magazines 38 may contain samples from multiple work-lists 26.

In the seventh step 407, the controller receives a list of empty wells 52 in each tray 54 in a column, row format. The wells 52 in each tray 54 form a grid consisting of columns and rows. The columns are designated with letters and the rows are designated with numbers. The wells 52 are placed in order such that the first well is A-1, the next well is A-2, and so on. After all the wells in column A, well B-1 comes next, and so on through all the wells in the tray 54.

In the eighth step 408, the user interface indicates at screen portion 375 (as shown in FIG. 21) the number of available wells 52 in each tray 54.

In the ninth step 409, the user interface queries the work-list 26 to determine which magazines 38 have samples associated with the work-list 26.

In the tenth step 410, the user interface indicates which magazines 38 have no samples associated with the work-list 26.

In the eleventh step 411, the user interface indicates which trays 54 are full and cannot receive additional samples.

In the twelfth step 412, steps two through eleven are repeated as necessary. Then the user begins the transfer of samples by clicking on the "Start Transfer" button 380 on the user interface, as shown in FIG. 21.

In the thirteenth step 413, the first empty well out of all of the trays 54 is determined based on the ordering of the wells 52 as described above. Because the tray receivers 220 cannot move independently of one another, the same well 52 in each tray 54 must be in the target position for each of the tray receivers 220. Therefore, all of the tray receivers 220 must be initially positioned for use based on the first empty well found in any of the trays 54. Each tray receiver 220 is moved such that the well 52 corresponding to the first empty well is placed in the target position.

In the fourteenth step 414, all of the magazines 38 are homed such that the first capsule 40 is positioned at the punch position 40'.

In the fifteenth step 415, each magazine 38 is advanced such that the capsule 40 containing the first sample to be transferred to the tray 54 is at the punch position 40'.

In the sixteenth step 416, for each tray 54, the corresponding sample removal station 140 punches the sample contained in the capsule 40 at the punch position 40' into the well 52 in the target position if the well 52 is empty, the well is not a control, and the capsule 40 contains a valid sample to be transferred to the well 52 in the target position as determined from the work-list 26.

In the seventeenth step 417, the user interface updates the work-list 26 to reflect newly emptied capsules 40 in the magazines 38 and newly full wells 52 in the trays 54.

In the eighteenth step 418, all of the tray receivers 220 are moved so that the next well 52 is in target position.

In the nineteenth step 419, each magazine 38 that just had a sample removed is advanced so the next capsule 40 is in the punch position 40'.

In the twentieth step 420, the user interface updates and displays each tray 54 that is now full.

In the twenty-first step 421, the user interface updates and displays each magazine 38 that is now empty.

In the twenty-second step 422, if all the trays 54 are full, the user interface displays all the trays 54 that are full and stops the cycling of the transfer station 50 as the twenty-seventh step 427.

In the twenty-third step 423, if all the magazines 38 are empty, the user interface displays all the magazines 38 that are empty and stops the cycling of the transfer station 50 as the twenty-seventh step 427.

In the twenty-fourth step 424, as long as the last well is not in the target position and is not full, steps sixteen through twenty-three are repeated as necessary.

In the twenty-fifth step 425, if the last well is in the target position and is full, at least one capsule 40 in one of the magazines 38 contains a sample to be transferred to one of the trays 54 according to the work-list 26, and at least one tray 54 contains an open well 52, then the transfer station 50 enters fill mode as the twenty-sixth step 426. If the no tray 54 contains an open well 52, then the cycling of the transfer station 50 stops as the twenty-seventh step 427.

Figure 23:
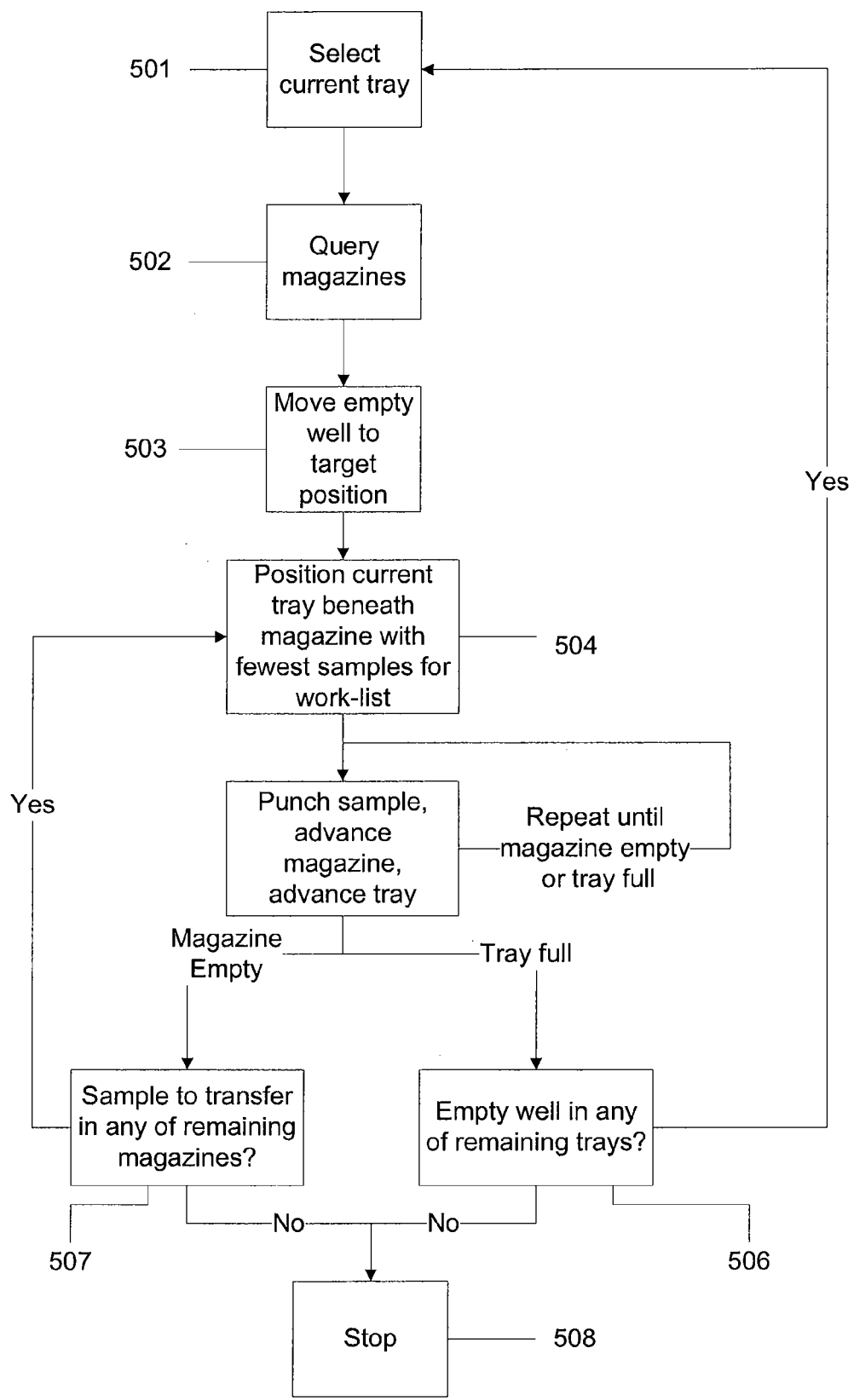
FIG. 23 is a flow-chart describing a process of the transfer station of FIG. 6.

As shown in FIG. 23, for fill mode step one 501, the transfer station 50 automatically selects the tray 54 with the fewest empty wells as the "current tray." For fill mode step two 502, the transfer station 50 queries each magazine 38 to determine if the magazine 38 contains samples for the current work-list 26. For fill mode step three 503, the tray receiver 220 with the selected tray 54 moves the first empty well in that tray 54 to the target position. For fill mode step four 504, the carousel 195 rotates such that the selected tray 54 is positioned beneath the magazine 38 with the fewest available samples for the work-list 26. For fill mode step five 505, the sample removal station 140 punches the sample contained in the capsule 40 at the punch position 40' into the well 52 in the target position, the controller updates the work-list accordingly, the magazine 38 advances the next capsule 40 to the punch position 40', and the tray receiver 220 moves so that the next empty well is in the target position. Fill mode step five 505 repeats until either the magazine 38 is empty or the selected tray 54 is full. For fill mode step six 506, if the tray 54 is full, the controller updates and, if any of the remaining trays 54 have at least one empty well 52, the transfer station 50 returns to fill mode step one. For fill mode step seven 507, if the magazine 38 is empty, the carousel 195 rotates such that the selected tray 54 is positioned beneath the non-empty magazine 38 with the fewest available samples for the work-list 26 and then the transfer station 50 returns to fill mode step four 504. For fill mode step eight 508, if all the trays 54 are full or no remaining magazine 38 contains a sample for the work-list 26, then the controller updates accordingly and the transfer station 50 stops cycling. Alternatively, a user could perform the steps of the fill mode.

Each source plant 20 is identified relative to a barcode or other identifier 22. This identification is linked to the capsule 40 that receives the sample of the plant during the sampling operation. The source plant 20 for the sample contained in each capsule 40 of a magazine 38 is then also identified by the capsule's 40 position in the magazine 38 relative to the register 42 and the magazine's barcode 39. Each well 52 in a tray 54 is designated in the column-row format and each tray 54 is identified by a barcode or other identifier 55. The transfer station 50 allows a sample to be transferred from a magazine 38 to a tray 54 according to work-list 26 thereby ensuring that the source plant associated with the sample contained in each well 52 of a tray 54 is known. After testing is conducted on the samples in the tray 54, a plant 20 can be selected based on its characteristics as determined by the testing.

Thus, the invention provides, among other things, methods and systems for transferring plant samples from a sampling device to a transfer station to facilitate testing of the samples. Various features and advantages of the invention are set forth in the following claims.

What is claimed is:

1. A system for processing plant material samples, the system comprising:
   a controller;
   a plant-material sampling device configured to communicate with the controller and to read an identifier of a plant, having a removable magazine, and for taking at least one plant sample from a plurality of plants, placing such samples in the magazine, and tracking the identity of the plant from which each sample is taken; and
   a transfer station configured to hold, at a plurality of positions, a plurality of magazines and a plurality of trays such that the positions of the plurality of magazines are mirrored by the positions of the plurality of trays, to read an identifier of each magazine, to read an identifier of each tray, to map storage locations for each one of the plurality of magazines to storage locations of one of the plurality of trays, and to sequentially unload plant samples from the plurality of magazines to the plurality of trays.

2. The system of claim 1, wherein the transfer station is configured to read a work-list.

3. The system of claim 1, wherein the transfer station is configured to track the identity of the plant from which each sample is taken from the plurality of magazines to the plurality of trays.

4. The system of claim 1, the transfer station further comprising:
   a plurality of magazine positions for holding the plurality of magazines; and
   a plurality of tray positions for holding the plurality of trays.

5. The system of claim 4, the transfer station further comprising:
   the plurality of magazine positions mounted to a platform; and
   the plurality of tray positions mounted to a rotatable carousel.

6. A method of processing plant material samples, the method comprising:
   collecting plant-material samples from a plurality of plants using a plant-material sampling device that
      is configured to communicate with a controller and to read an identifier of a plant, has a removable magazine, and
      tracks the identity of the plant from which each sample is taken; and
   transferring the plant material samples to a plurality of trays at a transfer station that
      is configured to hold, at a plurality positions, a plurality of magazines and a plurality of trays such that the positions of the plurality of magazines are mirrored by the positions of the plurality of trays,
      read an identifier of each magazine,
      read an identifier of each tray,
      map storage locations for each one of the plurality of magazines to storage locations of one of the plurality of trays, and
      sequentially unload plant materials from the plurality of magazines to the plurality of trays;
   performing tests on the plant material samples; and
   selecting certain of the plants for cultivation based on the tests.

7. The method of claim 6, the method further comprising: loading a work-list to the transfer station.

8. The method of claim 6, wherein the transfer station further comprises:
   a plurality of magazine positions for holding the plurality of magazines; and
   a plurality of tray positions for holding the plurality of trays.

9. The method of claim 8, wherein the transfer station further comprises:
   the plurality of magazine positions mounted to a platform; and
   the plurality of tray positions mounted to a rotatable carousel.

10. A transfer station, comprising:
    a plurality of magazine positions for holding a plurality of magazines;
    a scanner for reading an identifier on one of the plurality of magazines; and
    a plurality of tray positions for holding a plurality of trays such that the plurality of magazine positions are mirrored by the plurality of tray positions.

11. The transfer station of claim 10, wherein the each of the plurality of magazine positions is mounted to a platform and each of the plurality of tray positions is mounted to a rotatable carousel.

12. The transfer station of claim 11, wherein each magazine position includes a magazine receiver, a magazine indexer, and a punching rod assembly.

13. The transfer station of claim 11, wherein each tray position includes a tray receiver and a linear positioning slide.

14. The transfer station of claim 13, further comprising a scanner positioned near the carousel for reading an identifier on one of the plurality of trays.

15. The transfer station of claim 10, wherein the transfer station is configured to read a work-list.

* * * * *